US010869755B2

(12) United States Patent
Granada et al.

(10) Patent No.: US 10,869,755 B2
(45) Date of Patent: *Dec. 22, 2020

(54) REPLACEMENT CARDIAC VALVES AND METHODS OF USE AND MANUFACTURE

(71) Applicant: CEPHEA VALVE TECHNOLOGIES, INC., San Jose, CA (US)

(72) Inventors: Juan F. Granada, Upper Saddle River, NJ (US); Gary Erzberger, Minneapolis, MN (US); Michael P. Corcoran, Woodbury, MN (US); Dan Wallace, Santa Cruz, CA (US); Matteo Montorfano, Milan (IT); Alaide Chieffo, Milan (IT); Thierry Thaure, San Jose, CA (US); Aaron Grogan, Scotts Valley, CA (US); Peter Gregg, Santa Cruz, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,320

(22) Filed: Apr. 2, 2015

(65) Prior Publication Data

US 2016/0158000 A1 Jun. 9, 2016

Related U.S. Application Data

(60) Provisional application No. 62/089,719, filed on Dec. 9, 2014.

(51) Int. Cl.
*A61F 2/24* (2006.01)
*A61B 17/00* (2006.01)

(52) U.S. Cl.
CPC .............. *A61F 2/2409* (2013.01); *A61F 2/24* (2013.01); *A61F 2/243* (2013.01); *A61F 2/2418* (2013.01); *A61B 2017/00243* (2013.01); *A61F 2210/0019* (2013.01); *A61F 2220/0041* (2013.01); *A61F 2230/0006* (2013.01); *A61F 2230/0069* (2013.01); *A61F 2240/001* (2013.01);

(Continued)

(58) Field of Classification Search
CPC ........... A61F 2/24; A61F 2/2409; A61F 2/852
See application file for complete search history.

(56) References Cited

U.S. PATENT DOCUMENTS 3,334,629 A 8/1967 Cohn
3,409,013 A 11/1968 Henry
(Continued)

FOREIGN PATENT DOCUMENTS

CA 2859666 A1 6/2013
CN 1338951 A 3/2002
(Continued)

OTHER PUBLICATIONS

Granada et al.; U.S. Appl. No. 14/677,398 entitled "System and method for cardiac valve repair and replacement," filed Apr. 2, 2015.

(Continued)

*Primary Examiner* — Ann Schillinger
(74) *Attorney, Agent, or Firm* — Lerner, David, Littenberg, Krumholz & Mentlik, LLP

(57) ABSTRACT

Prosthetic mitral valves and their methods of manufacture and use.

32 Claims, 21 Drawing Sheets

(52) U.S. Cl.
CPC . *A61F 2240/002* (2013.01); *A61F 2250/0018* (2013.01); *A61F 2250/0036* (2013.01); *A61F 2250/0063* (2013.01)

(56) References Cited

U.S. PATENT DOCUMENTS

| | | | |
|---|---|---|---|
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,023 A | 11/1993 | Reger |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,405,377 A | 4/1995 | Cragg |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,183 A | 9/1996 | Nazari |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson et al. |
| 5,720,391 A | 2/1998 | Dohm et al. |
| 5,725,552 A | 3/1998 | Kotula et al. |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,957,973 A | 9/1999 | Quiachon et al. |
| 5,968,070 A | 10/1999 | Bley et al. |
| 5,984,957 A | 11/1999 | Laptewicz et al. |
| 5,984,959 A | 11/1999 | Robertson et al. |
| 5,984,973 A | 11/1999 | Girard et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson et al. |
| 6,093,203 A | 7/2000 | Uflacker |
| 6,113,612 A | 9/2000 | Swanson et al. |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |

(56) References Cited

U.S. PATENT DOCUMENTS

| | | |
|---|---|---|
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |
| 6,312,465 B1 | 11/2001 | Griffin et al. |
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,411,552 B1 | 6/2002 | Chiba |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg et al. |
| 6,712,842 B1 | 3/2004 | Gifford et al. |
| 6,712,843 B2 | 3/2004 | Elliott |
| 6,714,842 B1 | 3/2004 | Ito |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor et al. |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh et al. |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne et al. |
| 7,413,563 B2 | 8/2008 | Corcoran et al. |
| 7,445,631 B2 | 11/2008 | Salahieh et al. |
| 7,455,689 B2 | 11/2008 | Johnson |
| 7,500,988 B1 | 3/2009 | Butaric et al. |
| 7,566,336 B2 | 7/2009 | Corcoran et al. |
| 7,582,104 B2 | 9/2009 | Corcoran et al. |
| 7,591,848 B2 | 9/2009 | Allen |
| 7,625,364 B2 | 12/2009 | Corcoran et al. |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | LaFontaine |
| 7,748,389 B2 | 7/2010 | Salahieh et al. |
| 7,749,238 B2 | 7/2010 | Corcoran et al. |
| 7,780,725 B2 | 8/2010 | Haug et al. |

(56) References Cited

U.S. PATENT DOCUMENTS

| | | |
|---|---|---|
| 7,803,184 B2 | 9/2010 | McGuckin et al. |
| 7,803,186 B1 | 9/2010 | Li et al. |
| 7,824,442 B2 | 11/2010 | Salahieh et al. |
| 7,824,443 B2 | 11/2010 | Salahieh et al. |
| 7,896,915 B2 * | 3/2011 | Guyenot ............... A61F 2/2418 623/1.24 |
| 7,905,901 B2 | 3/2011 | Corcoran et al. |
| 7,927,351 B2 | 4/2011 | Corcoran et al. |
| 7,972,361 B2 | 7/2011 | Corcoran et al. |
| 8,043,368 B2 | 10/2011 | Crabtree |
| 8,057,540 B2 | 11/2011 | Letac et al. |
| 8,092,520 B2 | 1/2012 | Quadri |
| 8,167,935 B2 | 5/2012 | McGuckin et al. |
| 8,236,049 B2 | 8/2012 | Rowe et al. |
| 8,317,858 B2 | 11/2012 | Straubinger et al. |
| 8,366,741 B2 | 2/2013 | Chin et al. |
| 8,398,708 B2 | 3/2013 | Meiri et al. |
| 8,425,593 B2 | 4/2013 | Braido et al. |
| 8,444,689 B2 | 5/2013 | Zhang |
| 8,449,599 B2 | 5/2013 | Chau et al. |
| 8,551,132 B2 | 10/2013 | Eskridge et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 * | 11/2013 | Lane .................... A61F 2/2409 623/2.11 |
| 8,579,966 B2 | 11/2013 | Seguin et al. |
| 8,623,074 B2 | 1/2014 | Ryan |
| 8,628,566 B2 | 1/2014 | Eberhardt et al. |
| 8,673,000 B2 | 3/2014 | Tabor et al. |
| 8,685,080 B2 | 4/2014 | White |
| 8,721,708 B2 | 5/2014 | Sèguin et al. |
| 8,728,155 B2 | 5/2014 | Montorfano et al. |
| 8,740,962 B2 | 6/2014 | Finch et al. |
| 8,795,356 B2 | 8/2014 | Quadri et al. |
| 8,801,779 B2 | 8/2014 | Seguin et al. |
| 8,845,722 B2 | 9/2014 | Gabbay |
| 8,852,272 B2 | 10/2014 | Gross et al. |
| 8,870,948 B1 | 10/2014 | Erzberger et al. |
| 8,894,702 B2 | 11/2014 | Quadri et al. |
| 8,911,455 B2 | 12/2014 | Quadri et al. |
| 8,956,404 B2 | 2/2015 | Börtlein et al. |
| 8,986,375 B2 | 3/2015 | Garde et al. |
| 8,998,976 B2 | 4/2015 | Gregg et al. |
| 9,011,527 B2 | 4/2015 | Li et al. |
| 9,017,399 B2 | 4/2015 | Gross et al. |
| 9,023,074 B2 | 5/2015 | Theobald et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,060,857 B2 | 6/2015 | Nguyen et al. |
| 9,101,467 B2 | 8/2015 | Eberhardt et al. |
| 9,125,740 B2 | 9/2015 | Morriss et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,387,071 B2 | 7/2016 | Tuval et al. |
| 9,393,110 B2 | 7/2016 | Levi et al. |
| 9,393,112 B2 | 7/2016 | Tuval et al. |
| 9,414,852 B2 | 8/2016 | Gifford et al. |
| 9,414,913 B2 | 8/2016 | Beith et al. |
| 9,421,083 B2 | 8/2016 | Eidenschink et al. |
| 9,421,098 B2 | 8/2016 | Gifford et al. |
| 9,439,757 B2 | 9/2016 | Wallace et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,563 B2 | 11/2016 | Li |
| 9,486,306 B2 | 11/2016 | Tegels et al. |
| 9,492,273 B2 | 11/2016 | Wallace et al. |
| 9,498,330 B2 | 11/2016 | Solem |
| 9,504,564 B2 | 11/2016 | Nguyen et al. |
| 9,504,568 B2 | 11/2016 | Ryan et al. |
| 9,510,943 B2 | 12/2016 | Mesana et al. |
| 9,554,899 B2 | 1/2017 | Granada et al. |
| 9,561,103 B2 | 2/2017 | Granada et al. |
| 9,579,198 B2 | 2/2017 | Deem et al. |
| 9,655,722 B2 | 5/2017 | Morriss et al. |
| 9,883,941 B2 | 2/2018 | Hastings et al. |
| 9,949,824 B2 | 4/2018 | Bonhoeffer et al. |
| 10,004,601 B2 | 6/2018 | Tuval et al. |
| 10,433,953 B2 * | 10/2019 | Wallace ................. A61F 2/243 |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi et al. |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0074011 A1 | 4/2003 | Gilboa et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199971 A1 | 10/2003 | Tower et al. |
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey et al. |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127849 A1 | 7/2004 | Kantor |

(56) References Cited

U.S. PATENT DOCUMENTS

| | | |
|---|---|---|
| 2004/0127936 A1 | 7/2004 | Salahieh et al. |
| 2004/0127979 A1 | 7/2004 | Wilson et al. |
| 2004/0133232 A1 | 7/2004 | Rosenbluth et al. |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225354 A1 | 11/2004 | Allen et al. |
| 2004/0254636 A1 | 12/2004 | Flagle et al. |
| 2005/0033402 A1 | 2/2005 | Cully et al. |
| 2005/0038383 A1 | 2/2005 | Kelley et al. |
| 2005/0070934 A1 | 3/2005 | Tanaka et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0155312 A1 | 7/2006 | Levine et al. |
| 2006/0161249 A1 | 7/2006 | Realyvasquez et al. |
| 2006/0190030 A1 | 8/2006 | To et al. |
| 2006/0195183 A1 | 8/2006 | Navia et al. |
| 2006/0235510 A1 | 10/2006 | Johnson et al. |
| 2006/0247680 A1 | 11/2006 | Amplatz et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265045 A1 | 11/2006 | Shiu et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0203575 A1 | 8/2007 | Forster et al. |
| 2007/0244552 A1 | 10/2007 | Salahieh et al. |
| 2007/0255389 A1 | 11/2007 | Oberti et al. |
| 2007/0265656 A1 | 11/2007 | Amplatz et al. |
| 2007/0276324 A1 | 11/2007 | Laduca et al. |
| 2007/0288089 A1 | 12/2007 | Gurskis et al. |
| 2008/0015619 A1 | 1/2008 | Figulla et al. |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0140191 A1 | 6/2008 | Mathis et al. |
| 2008/0167682 A1 | 7/2008 | Corcoran et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0036768 A1 | 2/2009 | Seehusen et al. |
| 2009/0062841 A1 | 3/2009 | Amplatz et al. |
| 2009/0076598 A1 | 3/2009 | Salahieh et al. |
| 2009/0082803 A1 | 3/2009 | Adams et al. |
| 2009/0171456 A1 | 7/2009 | Kveen et al. |
| 2009/0182405 A1 | 7/2009 | De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1 | 2/2010 | Hill et al. |
| 2010/0049313 A1 | 2/2010 | Alon et al. |
| 2010/0094314 A1 | 4/2010 | Hernlund et al. |
| 2010/0114308 A1 | 5/2010 | Maschke |
| 2010/0121434 A1 | 5/2010 | Paul et al. |
| 2010/0161036 A1 | 6/2010 | Pintor et al. |
| 2010/0219092 A1 | 9/2010 | Salahieh et al. |
| 2010/0268204 A1 | 10/2010 | Tieu et al. |
| 2010/0280495 A1 | 11/2010 | Paul et al. |
| 2010/0284724 A1 | 11/2010 | Cardia |
| 2010/0298931 A1 | 11/2010 | Quadri et al. |
| 2010/0312333 A1* | 12/2010 | Navia ............... A61F 2/2418 623/2.36 |
| 2011/0004296 A1 | 1/2011 | Lutter et al. |
| 2011/0022157 A1 | 1/2011 | Essinger et al. |
| 2011/0034987 A1 | 2/2011 | Kennedy |
| 2011/0166636 A1 | 7/2011 | Rowe |
| 2011/0218619 A1 | 9/2011 | Benichou et al. |
| 2011/0245911 A1 | 10/2011 | Quill et al. |
| 2011/0257723 A1 | 10/2011 | McNamara |
| 2011/0264198 A1 | 10/2011 | Murray et al. |
| 2011/0295363 A1 | 12/2011 | Girard et al. |
| 2011/0301702 A1 | 12/2011 | Rust et al. |
| 2012/0016464 A1 | 1/2012 | Seguin |
| 2012/0059458 A1 | 3/2012 | Buchbinder et al. |
| 2012/0078360 A1 | 3/2012 | Rafiee |
| 2012/0101571 A1* | 4/2012 | Thambar ............ A61B 17/0057 623/2.17 |
| 2012/0101572 A1 | 4/2012 | Kovalsky et al. |
| 2012/0158129 A1 | 6/2012 | Duffy et al. |
| 2012/0197283 A1 | 8/2012 | Marchand et al. |
| 2012/0197391 A1 | 8/2012 | Alkhatib et al. |
| 2013/0041447 A1 | 2/2013 | Erb et al. |
| 2013/0041458 A1 | 2/2013 | Lashinski et al. |

(56) References Cited

U.S. PATENT DOCUMENTS

| | | |
|---|---|---|
| 2013/0253643 A1 | 9/2013 | Rolando et al. |
| 2013/0261737 A1 | 10/2013 | Costello |
| 2013/0282110 A1 | 10/2013 | Schweich, Jr. et al. |
| 2013/0282114 A1 | 10/2013 | Schweich, Jr. et al. |
| 2013/0304197 A1 | 11/2013 | Buchbnder et al. |
| 2013/0310923 A1 | 11/2013 | Kheradvar et al. |
| 2013/0331931 A1 | 12/2013 | Gregg et al. |
| 2014/0005771 A1 | 1/2014 | Braido et al. |
| 2014/0005775 A1 | 1/2014 | Alkhatib et al. |
| 2014/0005778 A1 | 1/2014 | Buchbinder et al. |
| 2014/0012368 A1* | 1/2014 | Sugimoto ............ A61L 31/022 623/2.11 |
| 2014/0012374 A1 | 1/2014 | Rankin |
| 2014/0052237 A1 | 2/2014 | Lane et al. |
| 2014/0052241 A1 | 2/2014 | Harks et al. |
| 2014/0052244 A1 | 2/2014 | Rolando et al. |
| 2014/0067048 A1 | 3/2014 | Chau et al. |
| 2014/0081383 A1 | 3/2014 | Eberhardt et al. |
| 2014/0107665 A1 | 4/2014 | Shellenberger et al. |
| 2014/0128726 A1 | 5/2014 | Quill et al. |
| 2014/0180391 A1 | 6/2014 | Dagan et al. |
| 2014/0214157 A1 | 7/2014 | Bortlein et al. |
| 2014/0214159 A1 | 7/2014 | Vidlund et al. |
| 2014/0222136 A1 | 8/2014 | Geist et al. |
| 2014/0236278 A1 | 8/2014 | Argentine et al. |
| 2014/0243954 A1 | 8/2014 | Shannon |
| 2014/0249622 A1 | 9/2014 | Carmi et al. |
| 2014/0257476 A1 | 9/2014 | Montorfano et al. |
| 2014/0277390 A1 | 9/2014 | Ratz et al. |
| 2014/0277563 A1 | 9/2014 | White |
| 2014/0324164 A1 | 10/2014 | Gross et al. |
| 2014/0330368 A1 | 11/2014 | Gloss et al. |
| 2014/0379076 A1 | 12/2014 | Vidlund et al. |
| 2015/0025623 A1 | 1/2015 | Granada et al. |
| 2015/0039083 A1 | 2/2015 | Rafiee |
| 2015/0045881 A1 | 2/2015 | Lim |
| 2015/0094802 A1 | 4/2015 | Buchbincler et al. |
| 2015/0112430 A1 | 4/2015 | Creaven et al. |
| 2015/0119637 A1 | 4/2015 | Alvarez et al. |
| 2015/0135506 A1* | 5/2015 | White ............ A61F 2/2418 29/428 |
| 2015/0142100 A1 | 5/2015 | Morriss et al. |
| 2015/0157457 A1 | 6/2015 | Hacohen |
| 2015/0173897 A1 | 6/2015 | Raanani et al. |
| 2015/0223773 A1 | 8/2015 | John et al. |
| 2015/0302634 A1 | 10/2015 | Florent et al. |
| 2015/0351903 A1 | 12/2015 | Morriss et al. |
| 2015/0351904 A1* | 12/2015 | Cooper ............ A61F 2/2418 623/2.1 |
| 2016/0038280 A1 | 2/2016 | Morriss et al. |
| 2016/0089234 A1 | 3/2016 | Gifford |
| 2016/0151153 A1 | 6/2016 | Sandstrom et al. |
| 2016/0158000 A1 | 6/2016 | Granada et al. |
| 2016/0158003 A1 | 6/2016 | Wallace et al. |
| 2016/0166384 A1 | 6/2016 | Olson et al. |
| 2016/0310269 A1 | 10/2016 | Braido et al. |
| 2017/0035569 A1 | 2/2017 | Deem et al. |
| 2017/0042675 A1 | 2/2017 | Freudenthal |
| 2017/0209261 A1 | 7/2017 | Bortlein et al. |
| 2017/0209269 A1 | 7/2017 | Conklin |
| 2017/0231762 A1 | 8/2017 | Quadri et al. |
| 2017/0245991 A1 | 8/2017 | Granada et al. |
| 2017/0325941 A1 | 11/2017 | Wallace et al. |
| 2017/0325948 A1 | 11/2017 | Wallace et al. |
| 2017/0354499 A1 | 12/2017 | Granada et al. |
| 2018/0000580 A1 | 1/2018 | Wallace et al. |
| 2018/0206983 A1 | 7/2018 | Noe et al. |
| 2018/0206984 A1 | 7/2018 | Noe et al. |
| 2018/0206985 A1 | 7/2018 | Noe et al. |
| 2018/0206986 A1 | 7/2018 | Noe et al. |
| 2018/0296341 A1 | 10/2018 | Noe et al. |

FOREIGN PATENT DOCUMENTS

| | | |
|---|---|---|
| EP | 0409929 B1 | 4/1997 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1469797 B1 | 11/2005 |
| EP | 1600121 A1 | 11/2005 |
| EP | 1616531 A2 | 1/2006 |
| EP | 1819304 A2 | 6/2006 |
| EP | 1849440 A1 | 10/2007 |
| EP | 2654624 A1 | 10/2013 |
| EP | 2124826 B1 | 7/2014 |
| WO | WO95/04556 A2 | 2/1995 |
| WO | WO95/29640 A1 | 11/1995 |
| WO | WO96/14032 A1 | 5/1996 |
| WO | WO96/24306 A1 | 8/1996 |
| WO | WO98/36790 A1 | 8/1998 |
| WO | WO98/57599 A2 | 12/1998 |
| WO | WO99/44542 A2 | 9/1999 |
| WO | WO00/09059 A2 | 2/2000 |
| WO | WO00/44308 A2 | 8/2000 |
| WO | WO00/44313 A1 | 8/2000 |
| WO | WO00/67661 A2 | 11/2000 |
| WO | WO01/05331 A1 | 1/2001 |
| WO | WO01/35870 A1 | 5/2001 |
| WO | WO01/64137 A1 | 9/2001 |
| WO | WO02/36048 A1 | 5/2002 |
| WO | WO02/41789 A2 | 5/2002 |
| WO | WO02/100297 A2 | 12/2002 |
| WO | WO03/003943 A2 | 1/2003 |
| WO | WO03/003949 A2 | 1/2003 |
| WO | WO03/011195 A2 | 2/2003 |
| WO | WO03/030776 A2 | 4/2003 |
| WO | WO03/015851 A1 | 11/2003 |
| WO | WO03/094797 A1 | 11/2003 |
| WO | WO2004/014256 A1 | 2/2004 |
| WO | WO2004/019811 A2 | 3/2004 |
| WO | WO2004/026117 A2 | 4/2004 |
| WO | WO2004/041126 A1 | 5/2004 |
| WO | WO2004/047681 A1 | 6/2004 |
| WO | WO2004/066876 A1 | 8/2004 |
| WO | WO2004/082536 A1 | 9/2004 |
| WO | WO2005/037361 A2 | 4/2005 |
| WO | WO2005/084595 A1 | 9/2005 |
| WO | WO2005/087140 A1 | 9/2005 |
| WO | WO2009/072122 A1 | 6/2009 |
| WO | WO2009/108615 A1 | 9/2009 |
| WO | WO2009/132187 A1 | 10/2009 |
| WO | WO2009/137755 A2 | 11/2009 |
| WO | WO2010/057262 A1 | 5/2010 |
| WO | WO2010/141847 A1 | 12/2010 |
| WO | WO2011/057087 A1 | 5/2011 |
| WO | WO2011/081997 A1 | 7/2011 |
| WO | WO2012/161786 A1 | 11/2012 |
| WO | WO2013/158608 A1 | 10/2013 |
| WO | WO2013/158613 A1 | 10/2013 |
| WO | 2013175468 A2 | 11/2013 |
| WO | WO2014/121280 A2 | 8/2014 |
| WO | WO2014/144247 A1 | 9/2014 |
| WO | 2014210124 A1 | 12/2014 |
| WO | WO2015/127283 A1 | 8/2015 |
| WO | 2017218877 A1 | 12/2017 |

OTHER PUBLICATIONS

Granada et al.; U.S. Appl. No. 14/677,334 entitled "Replacement cardiac valves and methods of use and manufacture," filed Apr. 2, 2015.

(56) References Cited

OTHER PUBLICATIONS

Granada et al.; U.S. Appl. No. 14/677,370 entitled "Replacement cardiac valves and methods of use and manufacture," filed Apr. 2, 2015.

Andersen et al.; Transluminal implantation of artificial heart valves. Description of a new expandable aortic valve and initial results with implantation by catheter technique in closed chest pigs; Euro. Heart J.; 13(5): 704-708; May 1992.

Atwood et al.; Insertion of Heart Valves by Catheterization; Project Supervised by Prof. S. Muftu of Northeastern University, May 2002: pp. 36-40.

Bodnar et al. Replacement Cardiac Valves R Chapter 13: Extinct cardiac valve prostheses. Pergamon Publishing Corporation. New York, 1991: 307-322 (year of pub. sufficiently earlier than effective US filing date and any foreign priority date).

Boudjemline et al. Percutaneous implantation of a biological valve in the aorta to treat aortic valve insufficiency—a sheep study.f Med Sci. Monit; Apr. 2002; vol. 8, No. 4: BR113-116.

Boudjemline et al. "Percutaneous implantation of a valve in the descending aorta in lambs." Euro. Heart J; Jul. 2002; 23: 1045-1049.

Boudjemline et al. "Percutaneous pulmonary valve replacement in a large right ventricular outflow tract: an experimental study." Journal of the Americal College of Cardiology; Mar. 2004; vol. 43(6): 1082-1087.

Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.

Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43 (4): 698-703.

Cribier et al. "Percutaneous Transcatheter Implantation of an Aortic Valve Prosthesis for Calcific Aortic Stenosis: First Human Case Description." Circulation; Dec. 2002; 106: 3006-3008.

Cribier et al. "Percutaneous Transcatheter Implantation of an Aortic Valve Prosthesis for Calcific Aortic Stenosis: First Human Case." Percutaneous Valve Technologies, Inc. 2002: 16 pages (year of pub. sufficiently earlier than effective US filing date and any foreign priority date).

Ferrari et al. "Percutaneous transvascular aortic valve replacement with self expanding stent-valve device." Poster from the presentation given at SMIT 2000, 12th International Conference. 1 pg. Sep. 5, 2000.

Hijazi "Transcatheter Valve Replacement: A New Era of Percutaneous Cardiac Intervention Begins." J. of Am. College of Cardio; Mar. 2004; 43(6): 1088-1089.

Huber et al. "Do valved stents compromise coronary flow?" European Journal of Cardio-thoracic Surgery; May 2004; vol. 25: 754-759.

Knudsen et al. "Catheter-implanted prosthetic heart valves." Int'l J. of Art. Organs; May 1993; 16(5): 253-262.

Kort et al. "Minimally invasive aortic valve replacement: Echocardiographic and clinical results." Am. Heart J; Sep. 2001; 142(3): 476-481.

Love et al. fThe Autogenous Tissue Heart Valve: Current Stat.f Journal of Cardiac Surgery; Dec. 1991; 6(4): 499-507.

Lutter et al. "Percutaneous aortic valve replacement: An experimental study. I. Studies on implantation." J. of Thoracic and Cardio. Surg; Apr. 2002; 123(4): 768-776.

Moulopoulos et al. "Catheter-Mounted Aortic Valves." Annals of Thoracic Surg; May 1971; 11(5): 423-430.

Paniagua et al. "Percutaneous heart valve in the chronic in vitro testing model." Circulation; Sep. 2002; 106: e51-e52.

Paniagua et al. Heart Watch (2004). Texas Heart Institute. Spring (March) 2004 Edition: 8 pages.

Pavcnik et al. "Percutaneous bioprosthetic veno valve: A long-term study in sheep." J. of Vascular Surg; Mar. 2002; 35(3): 598-603.

Phillips et al. "A Temporary Catheter-Tip Aortic Valve: Hemodynamic Effects on Experimental Acute Aortic Insufficiency." Annals of Thoracic Surg; Feb. 1976; 21(2): 134-136.

Sochman et al. "Percutaneous Transcatheter Aortic Disc Valve Prosthesis Implantation: A Feasibility Study." Cardiovasc. Intervent. Radiol: Sep.-Oct. 2000; 23: 384-388.

Stuart, M. "In Heart Valves, A Brave, New Non-Surgical World." Start-Up; Feb. 2004: 9-17.

Vahanian et al. "Percutaneous Approaches to Valvular Disease." Circulation; Apr. 2004; 109: 1572-1579.

Van Herwerden et al., "Percutaneous valve implantation: back to the future?" Euro. Heart J; Sep. 2002; 23(18): 1415-1416.

Zhou et al. "Self-expandable valved stent of large size: off-bypass implantation in pulmonary position." Eur. J. Cardiothorac; Aug. 2003; 24: 212-216.

Wallace et al.; U.S. Appl. No. 14/858,230 entitled "Replacement cardiac valves and methods of use and manufacture," filed Sep. 18, 2015.

Solvay; Novel revivent(tm) Myocardial anchoring system from bioVentrix uses solvay's zeniva® PEEK in tether component; 3 pages retrieved from the internet (http://www.solvay.com/en/media/press_release/20131205-novel-revivent-myocardial-anchoring-system-bioventrix-uses-zenivapeek.html); (Press Release); on Aug. 10, 2017.

Gregg et al.; U.S. Appl. No. 15/573,555 entitled "Cardiac valve delivery devices and systems," filed Nov. 13, 2017.

Granada et al.; U.S. Appl. No. 141/677,320 entitled "Replacement cardiac valves and methods of use and manufacture," filed Apr. 2, 2015.

Australian Search Report for Application No. 2015361260, dated Jul. 31, 2019, 1 pg.

Australian Search Report for Application No. 2019257514, dated Jul. 28, 2020, 1 page.

\* cited by examiner

REPLACEMENT CARDIAC VALVES AND METHODS OF USE AND MANUFACTURE

CROSS REFERENCE TO RELATED APPLICATIONS

This application claims priority to Provisional Application No. 62/089,719, filed Dec. 9, 2014, which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs are associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Minimally invasive aortic valve replacement devices, such as the Medtronic Corevalve or the Edwards Sapien, deliver aortic valve prostheses through small tubes which may be positioned within the heart through the aorta via the femoral artery or through the apex of the heart. However, current cardiac valve prostheses are not designed to function effectively within the mitral valve. Further, current cardiac valve prostheses delivered via a minimally invasive device are often difficult to place correctly within the native valve, difficult to match in size to the native valve, and difficult to retrieve and replace if initially placed incorrectly. Furthermore, the mitral valve differs from the aortic valve in that the shape and anatomy immediately surrounding the valve varies greatly from one side of the valve to the other. One access route for delivering replacement mitral valves requires a transseptal approach. Delivering a replacement valve transseptally imparts limitations on the size of the delivery device and the delivery profile of the replacement valve within the delivery device, and imparts certain flexibility requirements for the replacement valve itself as it is delivered transseptally to the location of the native mitral valve. In some embodiments a sheath passing through a septum should be at most about 24F-28F.

Many current minimally invasive valve devices are made from super-elastic Nickel-Titanium alloys. These super-elastic alloys allow high material strains, usually 6%-8%, without permanent deformation. Therefore, the alloys allow the valve devices to be packed into a small 6-10 mm diameter tube for delivery while expanding to around 50 mm within the heart. Current manufacturing methods typically involve cutting the valve prosthesis, at least the expandable anchor portion thereof, from a single tubular element that has a uniform thickness along its length. In these cases, the cut expandable anchor may have the same thickness along its length, and thus may not have varying stiffness along the length of the device. The inability to create an expandable anchor with varying thickness throughout can limit the functionality of different regions of the expandable anchor. Certain regions of the expandable anchor may be limited in what they can be configured to perform by creating the valve from a single tubular element. This can be undesirable if there is a need to create certain functionality in different regions of the expandable anchor that result from the regions have different thicknesses. Similarly, traditional expandable anchors made from a single tubular element do not have overlapping components (radially), wherein overlapping components may help impart additional flexibility to portions of the expandable anchor, and/or allow the expandable anchor to be collapsed to have a smaller delivery profile. Furthermore, in a single-piece construction, strains are limited to the elastic strain limit of the material, which may be too low for some applications.

These and other deficiencies in existing approaches are described herein.

SUMMARY OF THE DISCLOSURE

One aspect of the disclosure is a replacement mitral valve, comprising: a self-expandable anchor comprising a ventricular anchor, a central portion, and an atrial anchor, the self-expandable anchor having a self-expanded configuration in which the ventricular anchor and the atrial anchor are flared radially outward relative to the central portion such that the replacement mitral valve is configured to be secured within a mitral valve orifice, the ventricular anchor having greater stiffness in an axial direction than the atrial anchor when the expandable anchor is in the self-expanded configuration; and a plurality of replacement leaflets secured to the expandable anchor.

One aspect of the disclosure is a replacement mitral valve, comprising: a self-expandable anchor comprising a ventricular anchor integral with a central portion, and an atrial anchor secured to the central portion but not integral with the central portion, the self-expandable anchor having a self-expanded configuration in which the ventricular anchor and the atrial anchor are flared radially outward relative to the central portion such that the replacement mitral valve is configured to be secured within a mitral valve orifice; and a plurality of replacement leaflets secured to the expandable anchor.

One aspect of the disclosure is a method of manufacturing a replacement mitral valve, comprising creating a ventricular anchor integral with a central portion; securing an atrial anchor to the central portion, the atrial portion not integral with the central portion or the ventricular anchor; and forming a self-expandable anchor that has a self-expanded configuration in which the ventricular anchor and the atrial anchor are flared radially outward relative to the central portion such that the replacement mitral valve is configured to be secured within a mitral valve orifice.

One aspect of the disclosure is a replacement mitral valve, comprising a self-expandable anchor comprising a ventricular anchor comprising a plurality of ventricular arches, a central portion, and an atrial anchor comprising an annular frame with a plurality of atrial arches and a plurality of atrial apertures therethrough; the atrial anchor secured to the central portion and not integral with the central portion, the self-expandable anchor having a self-expanded configuration in which the ventricular anchor and the atrial anchor are flared radially outward relative to the central portion such that the replacement mitral valve is configured to be secured within a mitral valve orifice, wherein the central portion includes a plurality of central apertures therethrough, each of the plurality of atrial apertures in alignment with one of the plurality of central apertures to form a plurality of aligned apertures; a plurality of couplers, each of which extends through one of the plurality of aligned apertures and secures the central portion to the annular frame at the location of the aligned apertures; and a plurality of replacement leaflets secured to the expandable anchor.

One aspect of the disclosure is a method of manufacturing a replacement mitral valve, comprising: providing a central portion of an expandable anchor, the central portion including a plurality of central apertures therein that are disposed around a central opening; providing an atrial anchor that includes an annular frame comprising a plurality of atrial apertures therethrough; aligning each of the atrial apertures with a central aperture to form aligned apertures; extending a coupler through each of the aligned apertures from one side of the aligned apertures to a second side of the aligned apertures; plastically deforming each of the couplers to secure the central portion to the annular frame at the location of the couplers; and forming a self-expandable anchor that has a self-expanded configuration in which the ventricular anchor and the atrial anchor are flared radially outward relative to the central portion such that the replacement mitral valve is configured to be secured within a mitral valve orifice.

One aspect of the disclosure is a replacement mitral valve, comprising: a self-expandable anchor comprising a ventricular anchor, a central portion comprising a plurality of apertures therethrough that are disposed around the central portion, and an atrial anchor, the self-expandable anchor having a self-expanded configuration in which the ventricular anchor and the atrial anchor are flared radially outward relative to the central portion such that the replacement mitral valve is configured to be secured within a mitral valve orifice; an annular strut frame comprising a plurality of apertures therethrough around the strut frame, the strut frame disposed radially within the central portion, each of the plurality of annular strut frame apertures aligned with one of the plurality of central portion apertures, the annular strut frame secured to the central portion at the location of the plurality of strut frame apertures; and a plurality of replacement leaflets secured to the annular strut frame.

One aspect of the disclosure is a method of manufacturing a replacement mitral valve, comprising creating a ventricular anchor, a central portion, and an atrial anchor, the central portion including a plurality of apertures disposed around a central opening defined by the central portion; providing an annular strut frame, the strut frame comprising a plurality of apertures therethrough around the strut frame, positioning the annular strut frame radially within the central portion; aligning each of the plurality of strut frame apertures with an aperture on the central portion to create a plurality of overlapped apertures; providing a plurality of couplers, and extending a coupler through each of the plurality of overlapped apertures; plastically deforming the plurality of couplers to secure the central portion to the annular strut frame at the locations of the plurality of couplers; and forming a self-expandable anchor that has a self-expanded configuration in which the ventricular anchor portion and the atrial anchor portion are flared radially outward relative to the central portion such that the replacement mitral valve is configured to be secured within a mitral valve orifice.

DETAILED DESCRIPTION

Figure 1:
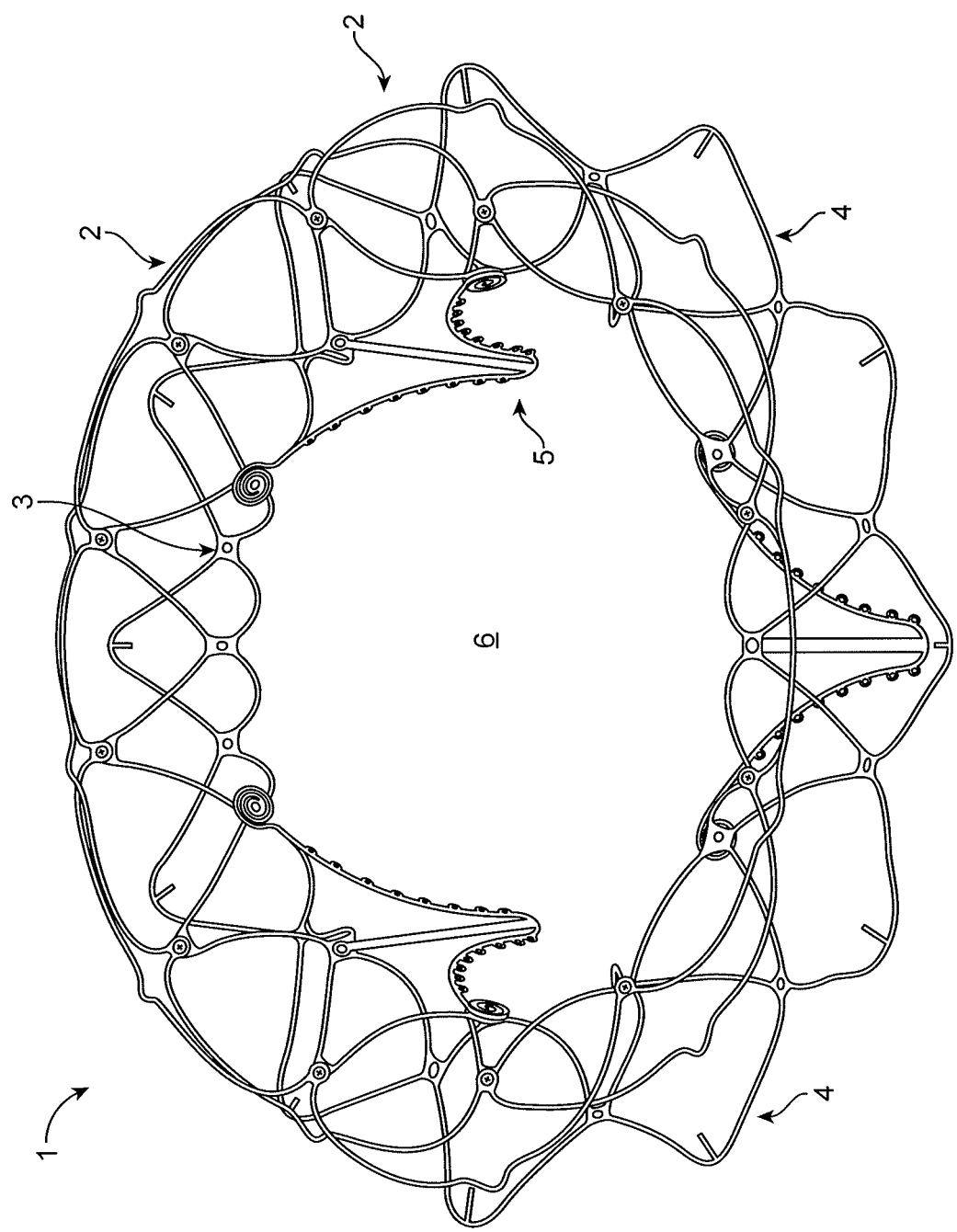
FIG. 1 shows a portion of an exemplary valve prosthesis in an expanded configuration.

This disclosure includes replacement heart valves (also referred herein as prosthetic heart valves), methods of manufacturing replacement heart valves, including subassemblies thereof, and methods of using replacement heart valves. This disclosure describes the prostheses in the context of replacement mitral valves, but it is conceivable that the prostheses herein can be used or modified to be used as other replacement heart valves. In some embodiments the replacement heart valves are self-orienting (at least on one side) replacement mitral valves configured to be delivered using minimally invasive techniques.

The replacement heart valves herein include an expandable anchor that includes an atrial anchor (e.g., configured to be placed on an atrial side of a mitral valve annulus), a ventricular anchor (e.g., configured to be placed on a ventricular side of a mitral valve annulus), and a central portion axially between the atrial and ventricular anchors. The expandable anchor is adapted to be collapsed towards a collapsed delivery configuration, and is adapted to expand towards an expandable configuration. The replacement heart valves also include a plurality of struts secured to at least one of the central portion, the ventricular anchor, or the atrial anchor, the struts being secured to a plurality of replacement leaflets. The struts can be considered part of the expandable anchor, and in embodiments herein are configured to deform as the rest of the expandable anchor is collapsed. It may be possible to incorporate struts that are not deformable, but which are still secured to the expandable anchor. These types of struts may not be considered part of the expandable anchor but are secured to the expandable anchor. The struts extend distally, that is, towards the ventricular anchor. In the context of replacement mitral valves, the "distal" end of the replacement valve refers to the end of the replacement valve that is to be positioned on the ventricular side of the annulus, while "proximal" end refers to the end of the replacement valve that is to be positioned on the atrial side of the annulus. "Distally" in the context of delivery can be used to refer to a location closer to the left ventricle than the left atrium, while "proximally" is generally used to refer to a location closer to the left atrium than the left ventricle.

In some embodiment the expandable anchor is adapted to completely self-expand, and in some embodiments it is configured to be partially self-expanding and partially expand by non-self-expanding influences (e.g., a balloon). The expandable anchors can be made of (or partly made of) a super elastic material such as nitinol.

One of the advantages of some of the replacement heart valves herein, and the methods of manufacturing provided herein, is that different regions of expandable anchors can have different physical characteristics that would not have been possible with alternative designs. For example, in some embodiments the expandable anchor is manufactured from two or more separate components of material that are secured together during manufacturing. By securing two or more different components together to create the expandable anchor, different starting materials can be used for the different components, and thus different materials with different properties can be used for different regions of the expandable anchor. The different properties can be chosen to impart desired physical characteristics to different regions of the expandable anchor.

When two components are secured together during manufacturing they are considered to be non-integral, or non-monolithic, components. Different portions of the expandable anchor that are made from the same starting material are considered to be integral, or monolithic. For example, a manufacturing step could include cutting a strut and an expandable anchor from different pieces of starting material, and securing them together, and they would be considered non-integral. In some embodiments, when one or more components are secured together, the coupling of the two components can be made so that the two components are rigidly secured at the coupling, or so that the two components can move to some degree at the location of the coupling of the two components (e.g., pivotable).

In methods of use, the prostheses described herein can be delivered to a cardiac valve orifice, such as the mitral valve, by using minimally invasive techniques to access the cardiac valve. Access routes and procedures are known, such as making small incisions in the patient's body and passing the prosthesis through the apex of the heart to, for example, a mitral valve. An additional exemplary access route includes delivering the valve through the venous system and into the left atrium via a transseptal puncture. A transseptal approach can impart size limitations on the delivery and thus the delivery profile of the replacement heart valve. Additionally, a transseptal approach can also impart certain flexibility requirements on the replacement heart valve. The replacement heart valves herein are configured to be collapsed into a delivery configuration so they can fit within a delivery device. The replacement heart valves can be delivered to the treatment site within the delivery device and then deployed from the delivery device. If necessary, the replacement valves can be repositioned, re-sheathed (partially or completely) if necessary, and then re-deployed.

When the replacement heart valve has been delivered near the mitral valve, the ventricular anchor can be deployed first in a cardiac chamber, such as the ventricle, and retracted to a seated position against the valve orifice, such as the mitral valve orifice. Then the center portion and atrial anchor portion may be deployed in another cardiac chamber, such as the atrium, wherein the expansion and reconfiguration of the atrial anchor and the central portion sandwiches the valve orifice securely between the anchors that have been deployed on either side of the annulus. Other exemplary aspects of the methods of delivery described in U.S. Pat. No. 8,870,948, issued Oct. 28, 2014 can be incorporated into any of the methods of delivery herein.

Replacement heart valves herein are configured to be secured in the native valve orifice by sandwiching the cardiac orifice between ventricular and atrial anchors, which are larger in diameter than the valve orifice, and by applying a radial force from the center portion outward against the cardiac orifice. Additional engagement between the prostheses and cardiac tissue can be added with wire hooks extending from the valve prostheses.

FIG. 1 is a perspective view of a portion of an exemplary mitral valve prosthesis in an expanded configuration after an expandable anchor and struts have been secured together. The portion of the replacement valve shown in FIG. 1 may be referred to as an anchor subassembly, which excludes leaflets and any skirts that may be incorporated into the final replacement valve. FIG. 1 shows a view from an atrial side to a ventricular side. Expandable anchor 1 includes an atrial anchor 2, a ventricular anchor 4, and a central portion 3 therebetween. In this embodiment atrial anchor 2 is configured and adapted to be disposed on an atrial side of a mitral valve orifice, and ventricular anchor 4 is configured and adapted to be disposed on a ventricle side of the mitral valve orifice. In some uses, however, anchor 1 may be implanted so that atrial anchor 2 as shown is positioned on the ventricle side and ventricular anchor 4 is positioned on the atrial side. Three struts 5 are secured to the expandable anchor, and in this embodiment are secured to central portion 3, and at least a portion of struts 5 are disposed radially inward relative to central portion 3. Struts 5 are extending, or pointing, towards ventricular anchor 4 and away from atrial anchor 2.

Radially inner surfaces of the expandable anchor and the struts define central opening 6, which is radially within the expandable anchor. The radially inner surfaces of central portion 3 substantially define the perimeter of central opening 6. Replacement leaflets, which are not shown in FIG. 1 for clarity, are secured to struts 5 and are disposed at least partially in central opening 6, and are configured to control blood flow therethrough.

Figure 2:
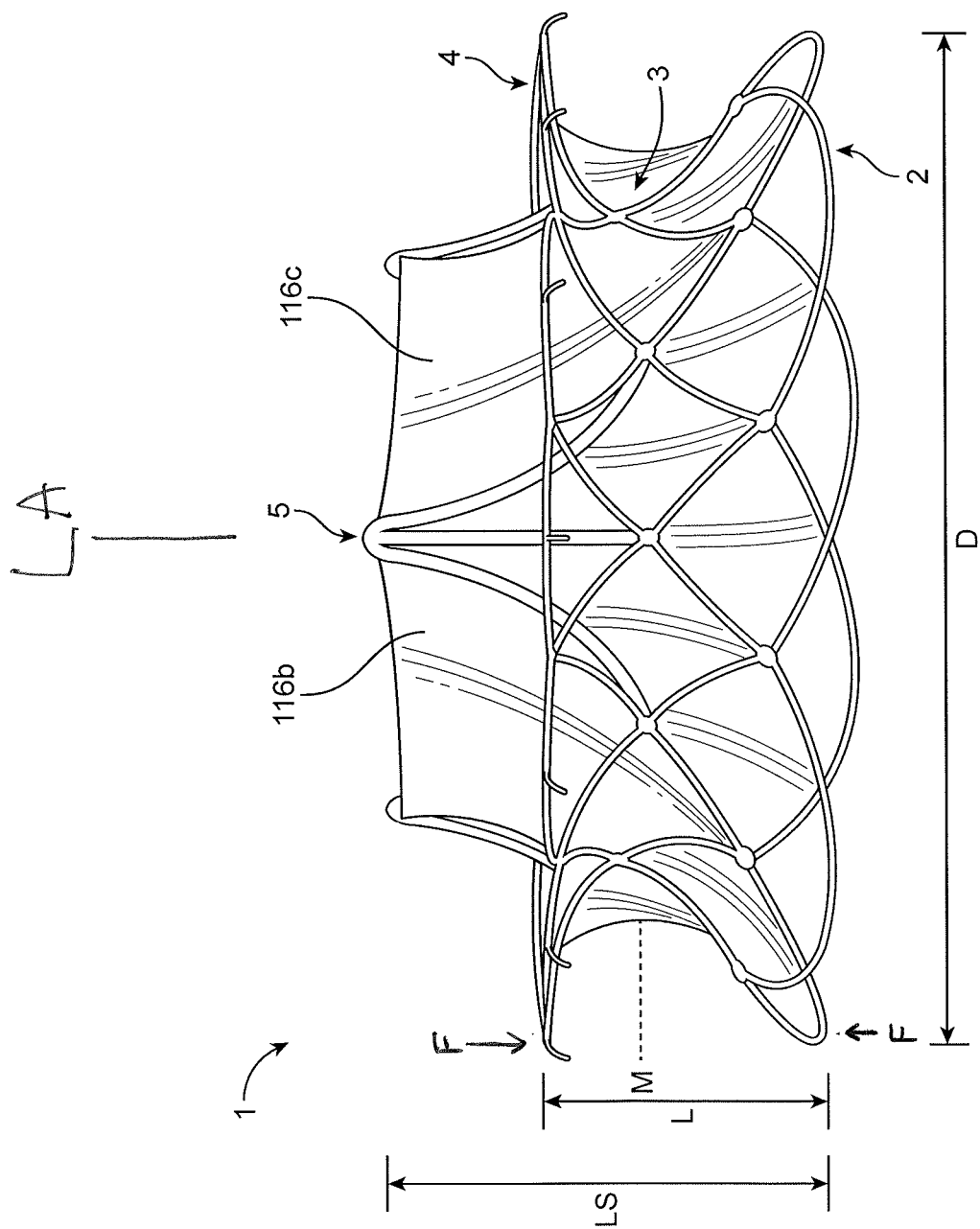
FIG. 2 is a side view illustrating an exemplary prosthesis including leaflets.

In the expanded configuration shown in FIG. 1 (which is also an "as-manufactured" configuration), atrial anchor 2 and ventricular anchor 4 extend radially outward from central portion 3, and are considered to flare outward relative to central portion 4. Atrial anchor 2 and ventricular anchor 4 can also be considered flanged relative to central portion 3. The flared configuration of atrial and ventricular anchors 2 and 4 relative to central portion 3 is described in the context of a side view of the expandable anchor, as can be seen in FIG. 2 (which illustrates leaflets secured to struts). In some embodiments one or more of the flared anchors are orthogonal to a longitudinal axis "LA" (illustrated in FIG. 2) passing through central opening 6. In some embodiments the flared anchor portions have a smooth curve radially outward. In some flared configuration the two anchors and the central portion define a general "C" or "U" shape in a side view of the expandable anchor. A "C" or "U" configuration is not limited to symmetrical configurations, however, as there can be slight deviation from a true "U" and still be considered to be U-shaped. For example, the expandable anchor could define a "C" configuration, but one of the atrial and ventricular anchors could have a tighter curvature than the other anchor. When the anchor portions are flared and create a "C" shaped configuration, the atrial and ventricular anchors are slightly curved inward towards the central portion at their respective ends. In some embodiments atrial anchor 2 and ventricular anchor 4 are substantially parallel to one another, such as exactly parallel to one another. In some embodiments the configuration of the flared anchors creates a substantially constant radius of curvature (i.e., a semi-circle) so that stress across anchors 2 and 4, and central portion 4 is balanced, thereby reducing fatigue or wear at any one point along the prosthesis.

In some embodiments the expanded anchor 1 (not including the struts) has a length "L" (see FIG. 2, measured from the atrial end to the ventricular end, parallel to the longitudinal axis LA) of 6-12 mm, such as 6-11 mm, 6-10 mm, 6-9 mm, 7-11 mm, 8-10 mm, 6 mm, 7 mm, 8 mm, 9 mm, 10 mm, 11 mm, and 12 mm. In some embodiments the length of the expanded prosthesis, including the struts ("LS" as shown in FIG. 2), has a length of 16-20 mm, such as 17-19 mm, 16 mm, 17 mm, 18 mm, 19 mm, and 20 mm with the struts. In some embodiments, the expanded anchor has an expanded diameter ("D" in FIG. 2) of about 35 mm to about 75 mm, such as about 45 mm to about 65 mm. In some of those embodiments the device is configured to be collapsed to a collapsed configuration in which it has a collapsed diameter D of 7 mm to 12 mm (i.e., the prosthesis can be collapsed down to fit within a 21-36 French catheter). In some embodiments the central opening 6 diameter ("DC" in FIG. 10A) is between 20 mm and 45 mm, such as between 25 mm and 40 mm, such as between 28 mm and 38 mm. In embodiments in which central opening 6 is not a perfect circle, the central opening diameter refers to the greatest linear dimension between points on the central portion, when viewed in an end view such as FIG. 10A.

Figure 3:
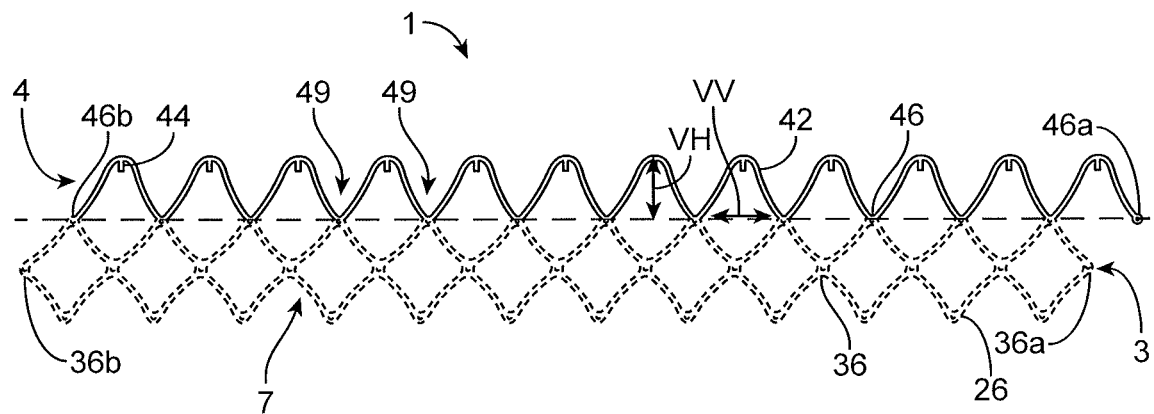
FIG. 3 illustrates an integral central portion and ventricular anchor after being cut from a sheet of material.

Additionally features of exemplary expandable anchor 1 will now be described in the context of an exemplary method of manufacturing the expandable anchor 1. Other manufacturing processes, whole or partial, can be used as well. FIGS. 3-6B illustrate an exemplary method of manufacturing a ventricular anchor 4 and central portion 3 that are integral, or monolithic. FIG. 3 illustrates integral central portion 4 and ventricular anchor 3 of expandable anchor 1 that have been cut (e.g., laser cut) out of a flat sheet of material. In some embodiments the material is a nitinol sheet, and in some exemplary embodiments the nitinol sheet is 0.3 mm to 0.35 mm thick. In these embodiments the ventricular anchor and central portion are thus 0.3 mm to 0.35 mm thick.

In this embodiment central portion 3, when cut, comprises a plurality of diamond-shaped cells 7 (only one labeled for clarity), as shown in the dotted lines in FIG. 3. In this embodiment there are twelve cells 7 in central portion 3, all of which have a general diamond shape when laid flat, as in the view shown in FIG. 3. Central portion 3 can have fewer or more cells, the cells can have configurations other than general diamond shapes, and the cells need not all have the same configuration. In this embodiment each central portion cell 7 has an aperture 26 at one of the bends in the diamond shape near the atrial end of central portion 3, but in other embodiments not every cell 7 has an aperture 26. For example, every other cell could have an aperture 26. In this embodiment apertures 26 are aligned axially (i.e., as shown they are in a "row"), but in other embodiments there are not. For example, if the cells have different configuration some apertures 26 may not be aligned, or in the same "row" with other apertures. Central portion 3 also includes a plurality of apertures 36 formed in material where adjacent cells 7 meet, as shown in FIG. 3. In this embodiment apertures 36 are axially aligned, but in other embodiments they need not be aligned. In this embodiment apertures 36 are in the middle of cells 7 measured in an atrial-to-ventricular end direction (up and down in FIG. 3).

Expandable anchor 1 also includes ventricular anchor 4. In this embodiment ventricular anchor 4 includes a plurality of arches 42 that extend from the central portion towards the ventricular end. The configurations of arches 42 are generally triangular-shaped, "pointing" towards the ventricular end, and include two sections of material and a bend in between the two sections of material. As shown, in each arch 42, the material first extends away from central portion 4, forms a bend at the ventricular end of the anchor, and then extends back towards central portion 4. Arches 42 are triangular shaped in this embodiment, and the ventricular ends can be described as tips of the arches, and in this embodiment are rounded. A plurality of spaces 49 (only two are labeled for clarity) between adjacent arches 42, the configurations and sizes of which are defined by the configuration of adjacent arches 42, are configured to advantageously allow the sub-valvular structures, such as chords, to slide between adjacent arches 42 when the ventricular anchor is expanded on the ventricular side of the mitral valve annulus. The configuration of arches 42, and thus the plurality of spaces 49, can also provide easier collapse of the ventricular anchor 3 radially inwards when the anchor is collapsed (e.g., for delivery). The arch 42 tips at the ventricular end are rounded, or curved (as opposed to abrupt or sharp) to avoid damaging the tissue when implanted. Additionally, the tip of each arch 42 includes optional hooks 44 extending from the tip. The hooks 44 can face in towards the central opening 15 and embed into the annulus tissue, thereby helping to resist the pressure build-up on the ventricular side of the aorta.

In some embodiments any of apertures 26, 36, and 46 can be circular. In some embodiments any of the apertures (such as all of them) can be between 0.3 mm and 0.8 mm in diameter, such as 0.4 mm-0.7 mm, 0.5 mm-0.6 mm, 0.3 mm, 0.4 mm, 0.5 mm, 0.6 mm, 0.7 mm, and 0.8 mm in diameter.

In the embodiment in FIG. 3 the same starting material is used to make the central portion 3 and ventricular anchor 4. In this embodiment ventricular anchor 4 and central portion 4 are cut from a flat sheet of material (e.g., nitinol). In other embodiments the integral central portion 3 and ventricular anchor 4 can be cut from a tubular starting material. After ventricular anchor 4 and central portion 3 are cut as shown in FIG. 2, a next step in manufacturing the expandable anchor is that it is then rolled into a generally cylindrical configuration and the ends of the material are secured together, as shown in the generally cylindrical configuration in the perspective view of FIG. 4. In this embodiment apertures 36a and 36b, and 46a and 46b, (FIG. 3) are secured together once the apparatus is reconfigured into the cylindrical configuration in FIG. 4. An exemplary method of securing the ends is by riveting the ends at the apertures, wherein a rivet is placed within aligned apertures 36a and 36b, and then the free rivet end is deformed to secure the ends of the apparatus and maintain the cylindrical configuration shown in FIG. 4.

Figure 4:
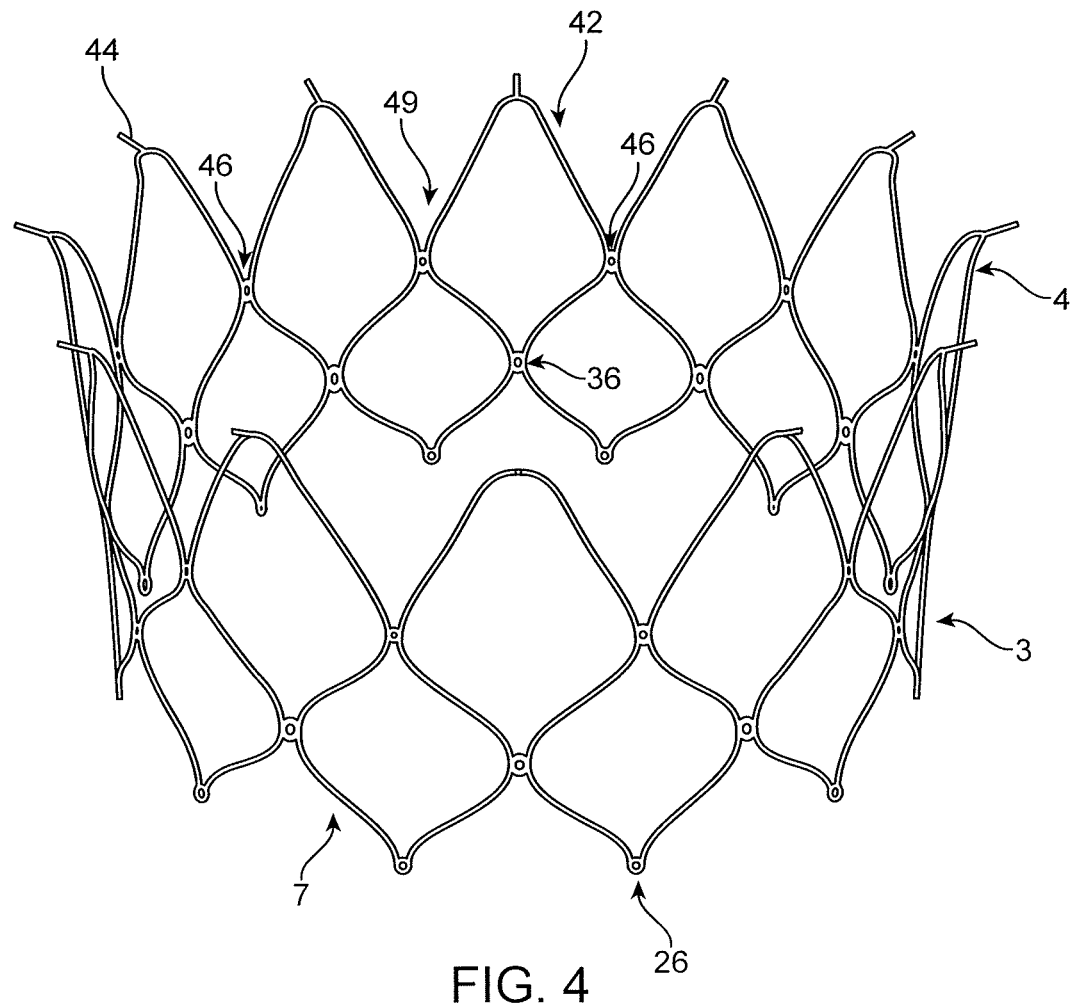
FIG. 4 is a perspective view illustrating an integral central portion and ventricular anchor after being rolled with ends secured.

Alternatively, in some embodiments, integral central portion 3 and ventricular anchor 4 can be cut from a tubular element to form the configuration in FIG. 4. In these embodiments ends of the device need not be coupled together since the apparatus has the configuration in FIG. 3 when cut from the tubular element.

Figure 5A:
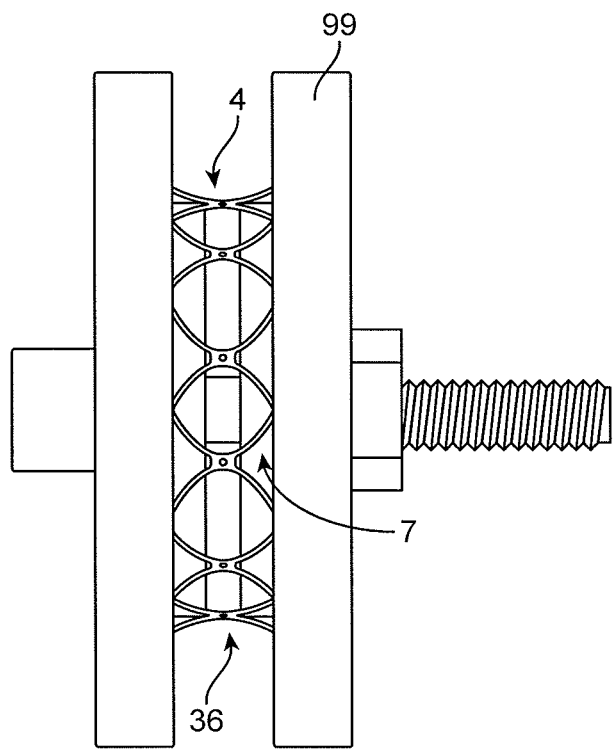
FIGS. 5A and 5B show formation of an expanded configuration of an integral central portion and ventricular anchor using a heat shaping fixture.
Figure 5B:
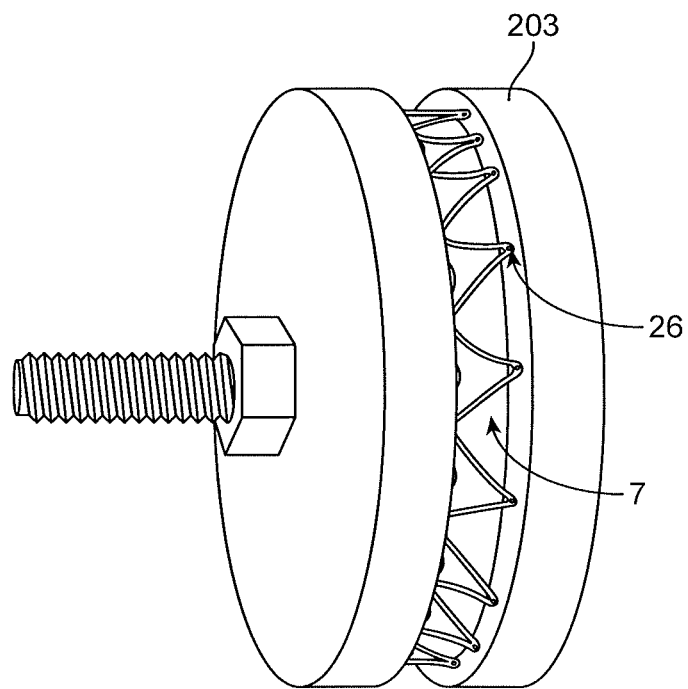
Figure 6A:
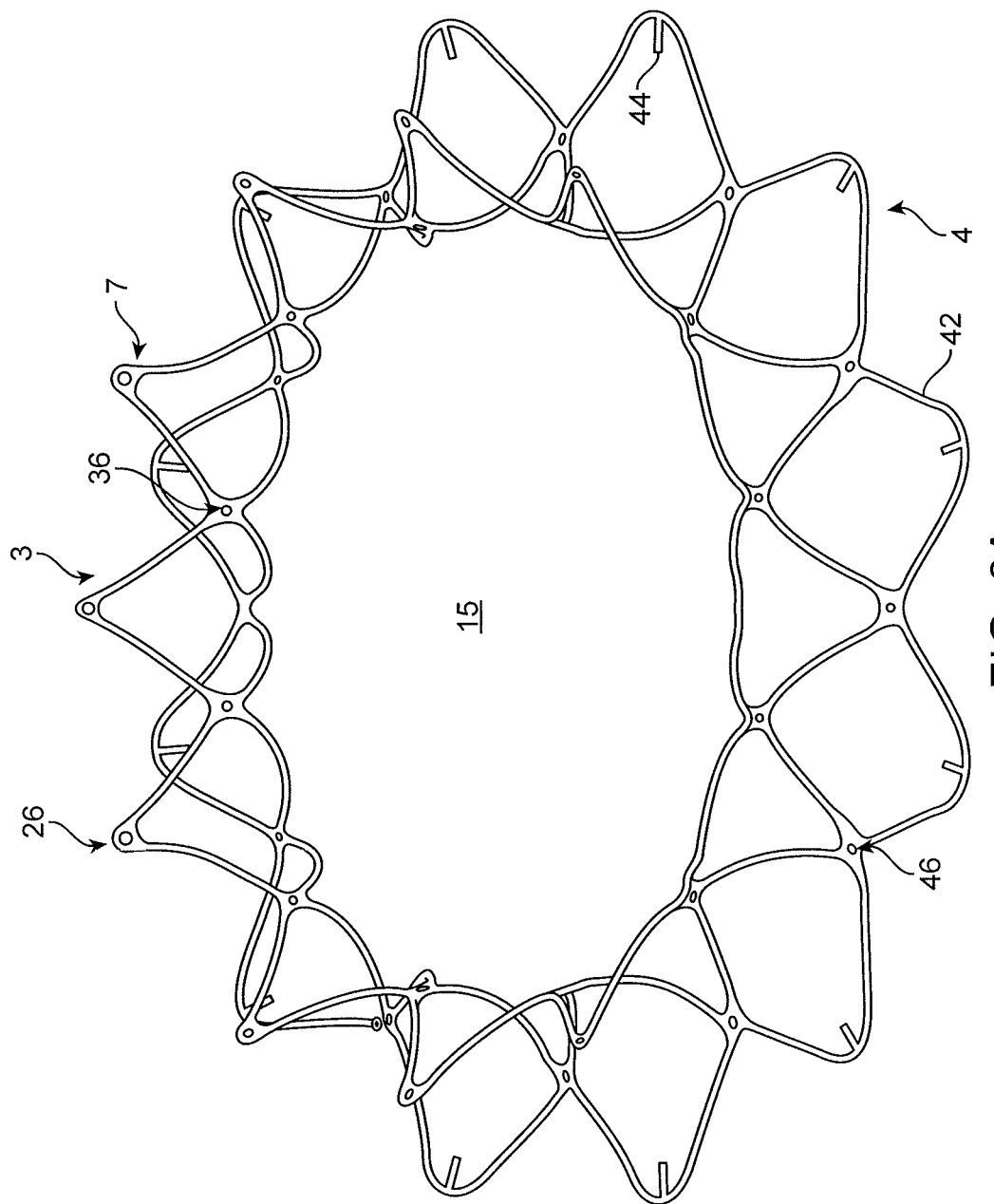
FIGS. 6A and 6B show an integral central portion and ventricular anchor after being shape set in an expanded configuration.
Figure 6B:
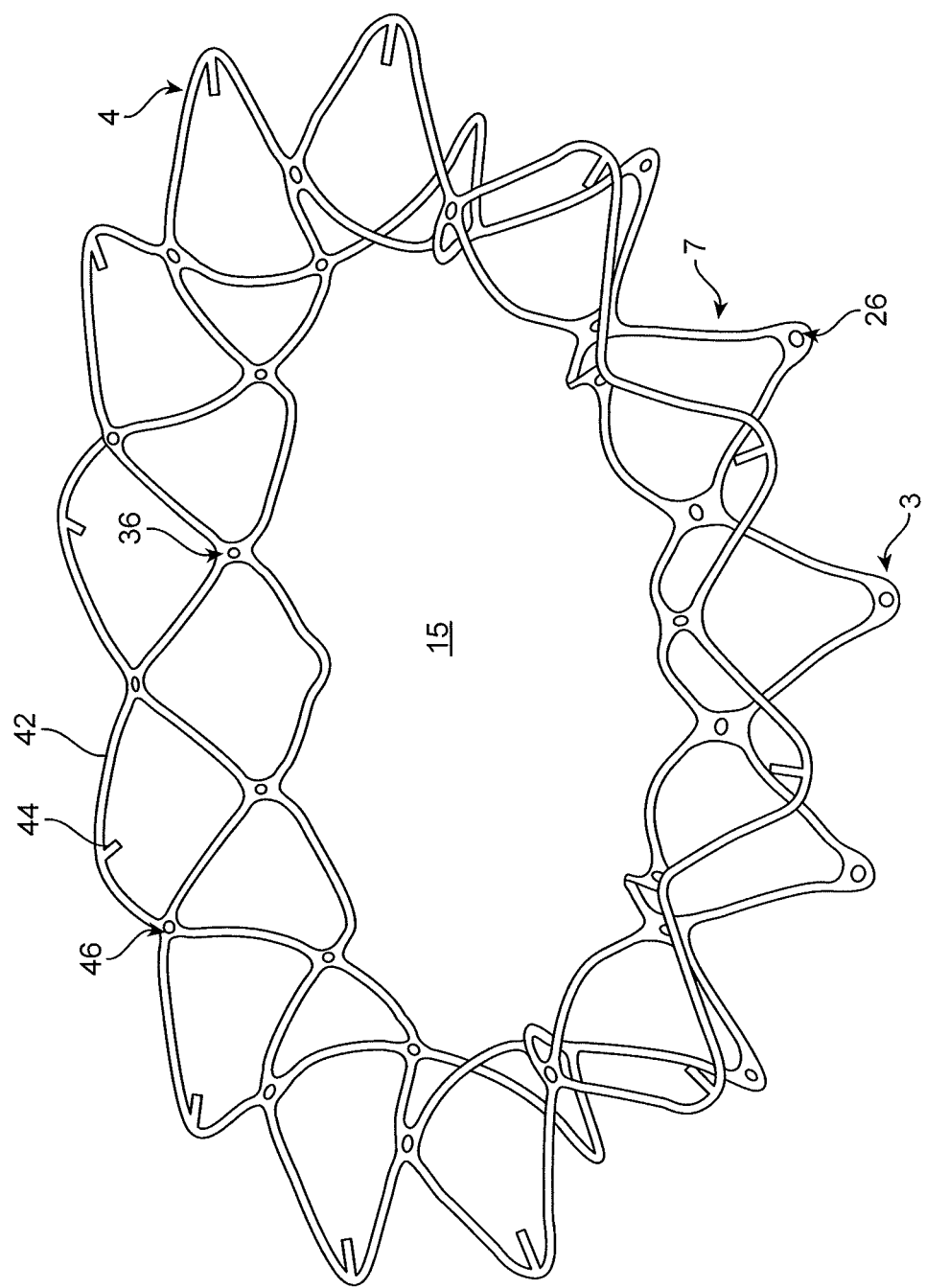

Once the apparatus is in the cylindrical configuration shown in FIG. 4 (whether cut from a flat sheet and rolled, or cut from a tubular element, or from another process), an exemplary subsequent step is to reshape the partial anchor into a shape memory configuration. FIGS. 5A-6B illustrate an exemplary shaping process and resulting reconfigured apparatus. As shown in FIGS. 5A and 5B, the generally cylindrical shaped device is placed in a heat shaping fixture 99. Once in the heat shaping fixture, the column can be heated, such as in a salt bath at 915 degrees for 3 minutes, and then quenched in water in order to set the shape of the ventricular anchor and central portion. The shape memory configuration of the integral central portion 3 and ventricular anchor 4 are shown in the perspective views in FIGS. 6A and 6B. FIG. 6A shows a perspective view looking from the central portion to the ventricular anchor, and FIG. 6B shows a view looking from the ventricular anchor to the central portion. The reference numbers in FIGS. 6A and 6B are described herein. A side view of the configuration of the anchor from FIGS. 6A and 6B can also be seen in the replacement valve in FIG. 2, but the atrial anchor and leaflets have not been added yet to the partial device shown in FIGS. 6A and 6B.

Figure 7B:
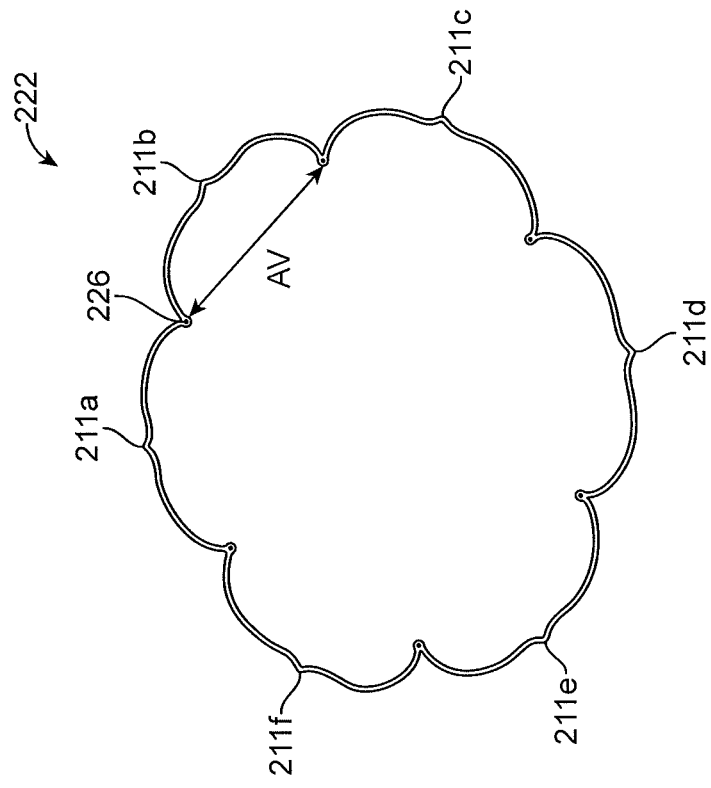
FIGS. 7A and 7B illustrate atrial frames of an atrial anchor.
Figure 7A:
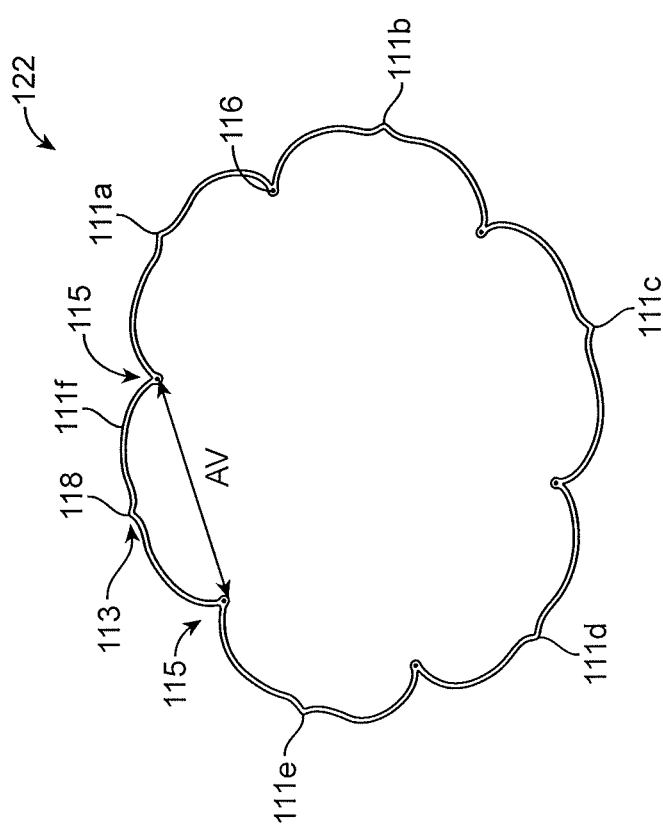

In this exemplary embodiment, once the integral ventricular anchor 4 and central portion 3 are shape set (as shown in FIGS. 6A and 6B), atrial anchor 2 is secured to central portion 3. In this embodiment atrial anchor 2 comprises first frame 122 and second frame 222, which are shown in FIGS. 7A and 7B, respectively. In this embodiment frame 122 and 222 have the same configuration and are interchangeable. In this embodiment second frame 222 is an inner frame, and first frame 122 is an outer frame in that first frame 122 is disposed radially outward relative to inner frame 222. Inner frame 222 also sits proximal to outer frame 122, although in this embodiment the two atrial frames have the same configuration and thus their designation of inner and outer can be switched.

As shown in FIGS. 7A and 7B, atrial frame 122 includes a plurality of arches 111a-111f (also referred to herein as arcs, arcuate portions, curved portions, or petals), and atrial frame 222 includes a plurality of arches 211. In this embodiment each arch 111 includes a peak 113, and adjacent arches meet at valleys 115 (only one peak and two valleys labeled for clarity). A peak is generally considered the location where the radial distance from the valley is greatest. In this embodiment there are six peaks and six valleys in each of frames 122 and 222. In this embodiment each frame includes apertures disposed at each of the frame valleys. Frame 122 includes six apertures 116 (one labeled), in this embodiment one at each valley 115. Frame 222 includes six apertures 226, one at each valley. In other embodiments a frame may include more or fewer arches, such as between two and fifteen arches.

Atrial frame 222 includes arches 211a-211f, each comprising a peak, and valleys one either side of a peak. The arches 211 meet at the valleys, each of which has an aperture 226 therethrough. In this embodiment all of the arches, on both of frames 122 and 222, comprise a protuberance or extension 118 (only one protuberance labeled, which is on frame 122 in FIG. 7A) near the center, or midline, of each arch. The midline is the middle of the length of the arch, as measured linearly between valleys on either side of the arch. The protuberance is a portion of the arch that has increased curvature relative to adjacent portions of the arch. During collapse of the prosthesis, the protuberances 118 can be pulled upon, providing easier collapse and reducing strain in the arches when the anchor is collapsed (e.g., for delivery).

In some embodiments either or both of atrial frames 122 and 222 are cut out of a flat sheet, such as a sheet of nitinol, as in the case in FIGS. 7A and 7B. In some embodiments the sheet of nitinol is 0.2 to 0.25 mm thick, which results in frames that are 0.2 mm to 0.25 mm thick. In this embodiment all of the arches on each frame are integral, or made from the same starting material. Frames 122 and 222 have an annular configuration, as can be seen in FIGS. 7A and 7B, even though they are not perfectly annular. Annular in this context refers to structures (e.g., atrial frames) that, once assembled as part of the expandable anchor, subtend 360 degrees around a longitudinal axis LA of the expandable frame. In other words, they are generally annular even though they are not perfectly annular. A longitudinal axis as used herein does not impart symmetry to the replacement heart valve, but generally refers to an axis that passes through a central portion of the central opening in the expandable anchor.

Figure 8:
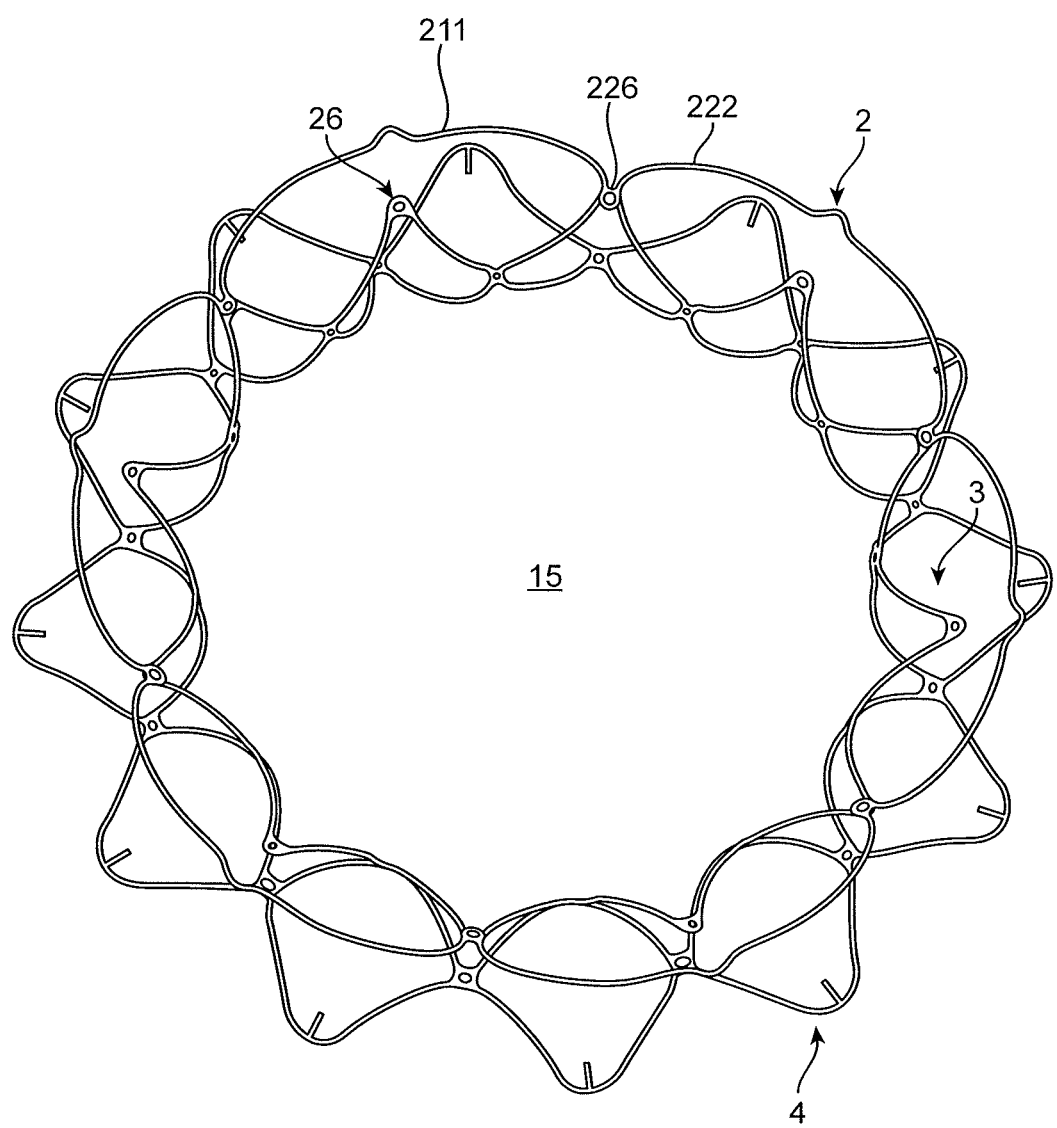
FIG. 8 illustrates an atrial frame of an atrial anchor secured to a central portion.

In the manufacturing of the expandable anchor, atrial frames 122 and 222, once formed (e.g., cut), are secured to central portion 3. In this embodiment there are twelve apertures 26 at one end of central portion 3, as can be seen clearly in FIG. 3. Each of frames 122 and 222 has six apertures 116 and 226, respectively, and in this embodiment each one disposed in a valley of the frame between arches. To secure atrial frame 222 to central portion 3, each aperture 226 is aligned with an aperture 26 in central portion, the relative positions of which can be seen in FIG. 8. FIG. 8 shows frame 222 assembled to central portion 3 at a plurality of aligned apertures. In this embodiment frame 222 and central portion 3 are configured, including the location of the apertures, such that apertures 226 on frame 222 are aligned with alternating apertures 26 in central portion 3, as shown in FIG. 8. In this embodiment frame 222 and central portion 3 are secured together at the location of the aligned apertures by riveting the components together at the locations of the apertures. A rivet is placed through two aligned apertures, and then one side of the rivet is plastically deformed to secure the atrial frame to the central portion at the location of the aligned apertures.

Figure 9:
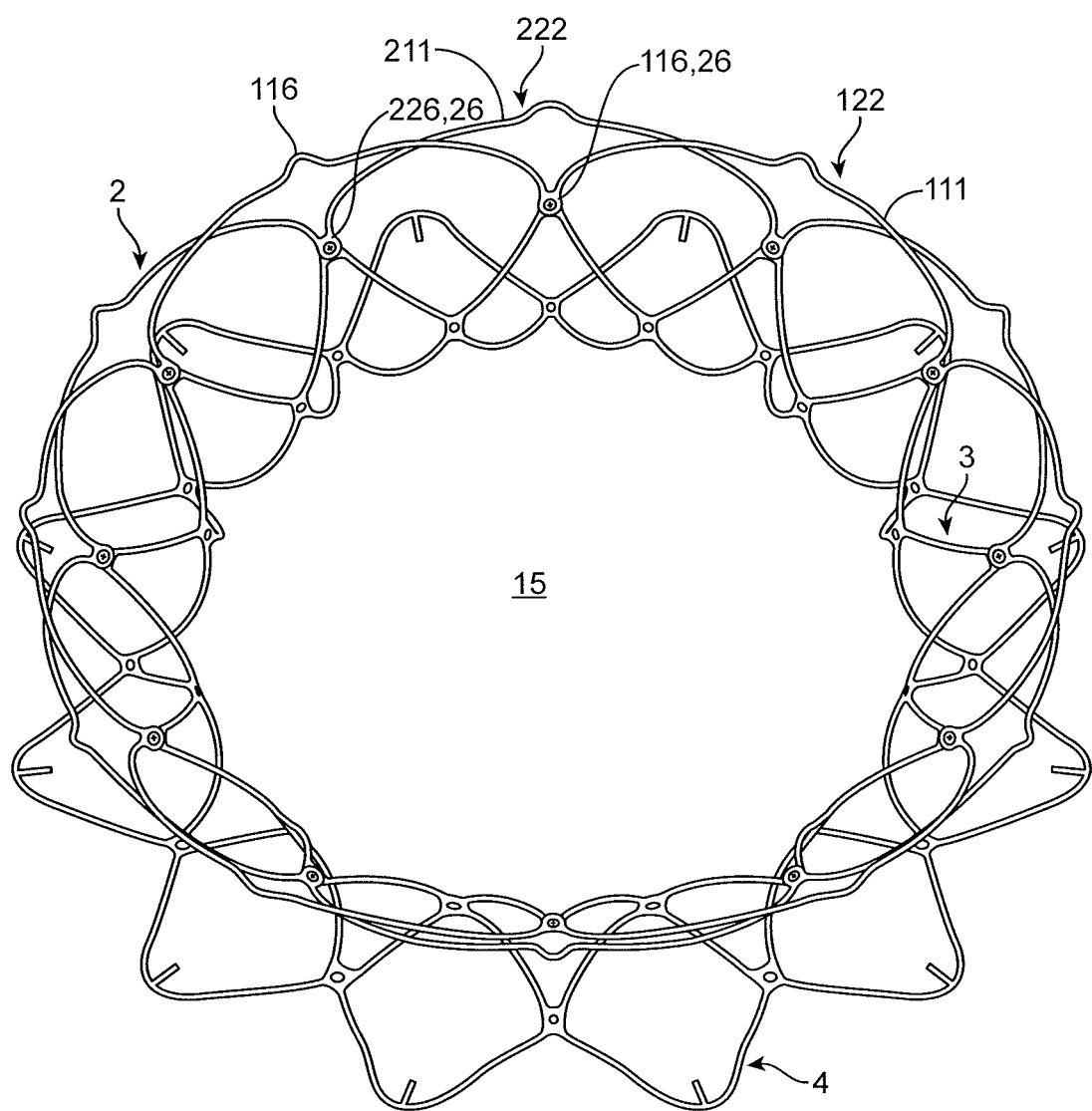
FIG. 9 illustrates an expanded anchor after a second atrial frame of an atrial anchor has been secured to the central portion.

After frame 222 is secured to central portion 3 (which can be seen in FIG. 8), frame 122 is secured to central portion 3 in the same manner, except in this embodiment the six apertures 116 in frame 122 are first aligned with the six apertures 26 that are not yet riveted to frame 222 (the six "open" apertures 26 can be seen in FIG. 8). FIG. 9 shows the expandable anchor after frame 122 is secured to central portion 3, which in this embodiment is also done with rivets like frame 222. Frames 122 and 222 are rotationally offset with one another with respect to central portion (which can be seen in FIG. 9), and in this embodiment the peaks of one frame are rotationally aligned with a valley of the other frame. Frames 122 and 222 overlap at frame sections between the valleys and peaks, and are in contact with one another where they overlap (but in other embodiments the memory configuration may be such that frame are slightly apart such that they do not contact one another where they overlap), which can be seen in FIG. 9. In this embodiment the frames overlap between the peaks and valleys. In this configuration arches 111 and 211 of the two frames are considered to be out of phase relative to one another, as can be seen in FIG. 9. For example, arches 111 can be approximately 30 degrees out of phase relative to arches 211. That is, arches 111 of the first frame 122 can overlap with arches 211 of the second frame 222 such that, for example, a single arch 111 of the first outer frame 122 overlaps with half of two underlying arches 211 of the second outer frame 222. In some embodiments, only some arches are out of phase with one another while other arches are in-phase with one another. When frames 122 and 222 are secured to central portion 3, the combination of overlapping frames 122 and 222 can form a substantially circular, or annular, outer perimeter (in an end view of the device such as in FIG. 9), which can provide a smooth surface to sit against the atrial tissue.

Frames 122 and 222 are secured to central portion 3, but they are not directly attached to one another. This configuration allows for relative movement between frames 122 and 222. The relative movement around atrial anchor 2 may allow for atrial anchor 2 to conform better to the tissue on the atrial side of the annulus (there may be patient to patient variability) and help seal the expandable anchor in place better on the atrial side. For example, an arch 111 can be movable relative to the two arches 211 that it overlaps. That is, the outer perimeter of an arch 111 can flex in the direction of the longitudinal axis (axially) and/or translate relative to the two arches 211 that it overlaps, while the radially inner portions of the frames are secured to the central portion of the expandable anchor. The outer perimeter of the atrial anchor essentially creates a substantially circular, or annular, flexible seal whose arches can flex as needed relative to overlapping arches to better conform to the patient's anatomy and help create a better seal against atrial tissue.

Figure 10:
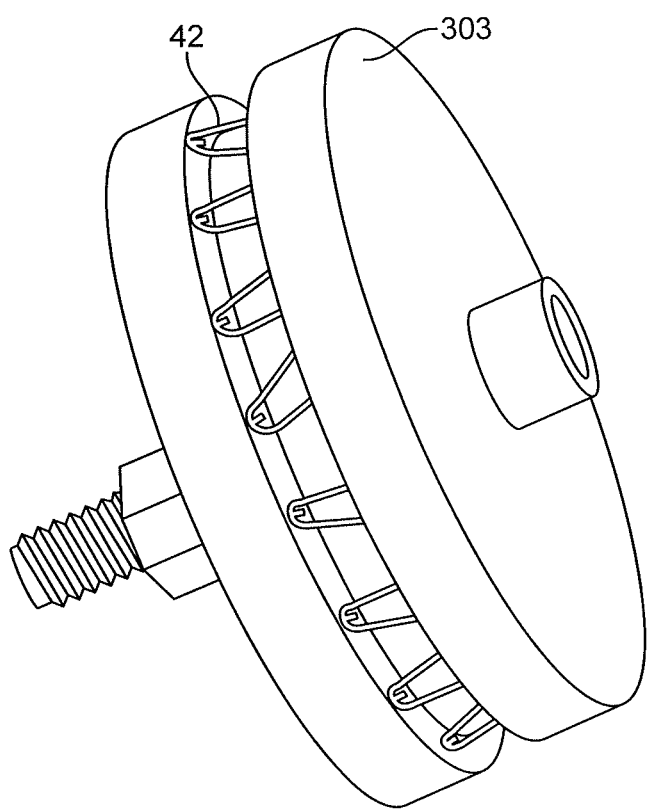
FIG. 10 shows formation of an expandable anchor after the atrial anchor has been secured thereto, using a heat shaping fixture.

After atrial anchor 2 is attached to central portion 3 (shown in FIG. 9), the expandable anchor can be heat shaped again. FIG. 10 shows the expandable anchor (ventricular anchor 4 arches 42 can be seen in FIG. 10) after it is placed into a shaping fixture 303 and heated, such as at 915 degrees for 3 minutes, and then quenched in water to form the expandable anchor. The configuration of the expandable anchor after this shape setting step is shown in FIGS. 11A and 11B, with reference numbers described above.

Figure 11A:
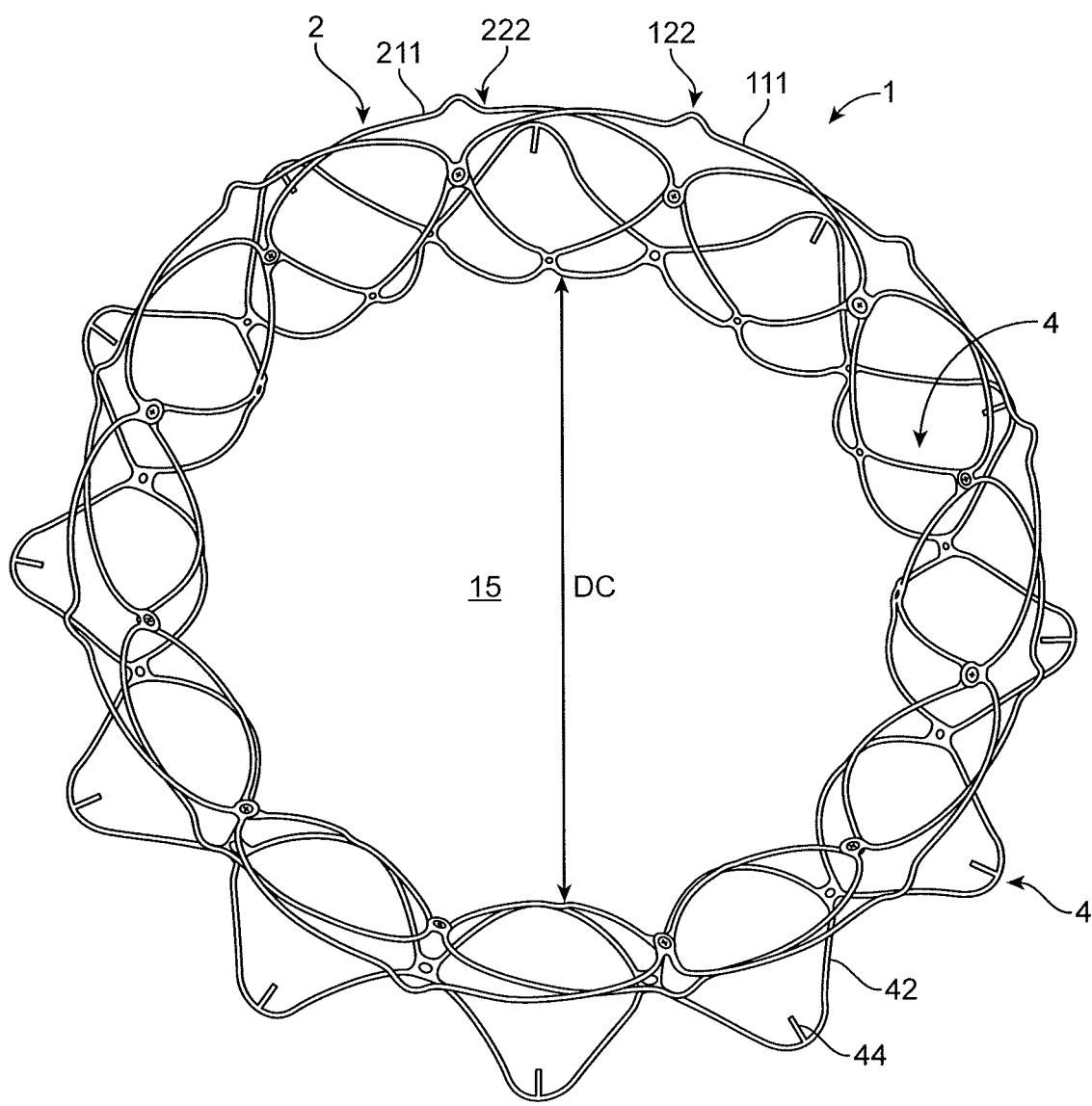
FIGS. 11A and 11B illustrate an expandable anchor in an expanded configuration before struts have been secured thereto.
Figure 11B:
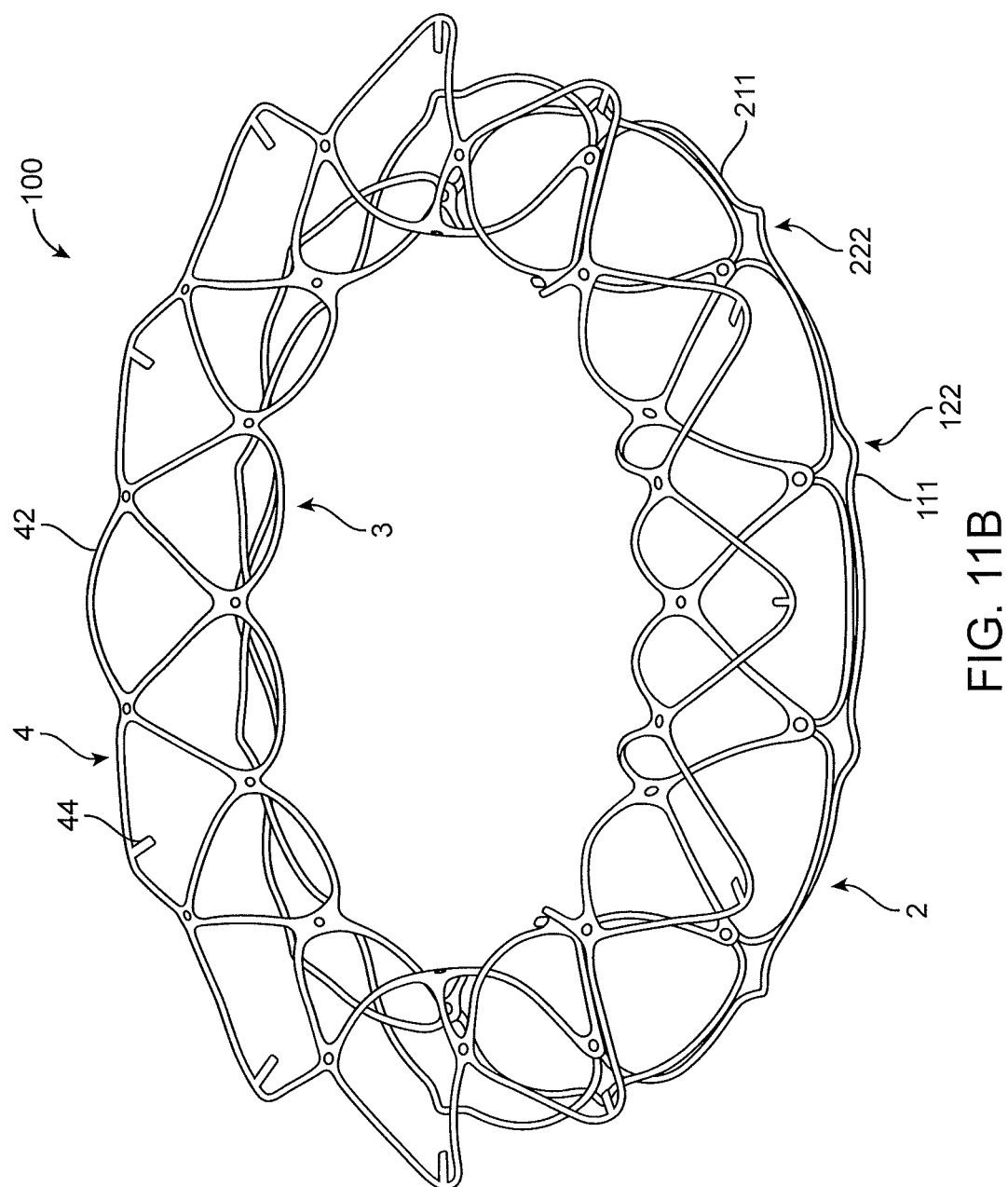

The exemplary expandable anchor shown in FIGS. 11A and 11B, which is shown in an expanded memory configuration, has a ventricular anchor and an atrial anchor that are flared radially outward relative to the central portion such that the self-expandable anchor is configured to secure the replacement mitral valve to a mitral valve orifice in the self-expanded configuration. In this embodiment ventricular anchor 4, which includes plurality of arches 42, has a greater stiffness in the axial direction than the atrial anchor when the expandable anchor is in the expanded configuration. FIG. 2 illustrates hypothetical axially forces "F" applied to the ventricular and atrial anchors, upon which ventricular anchor 4 has a greater resistance to deformation than atrial anchor 2. The stiffness comparison is generally considered in response to a hypothetical applied force on the radially outer portions of the ventricular and atrial anchors, as shown by forces F in FIG. 2.

One aspect of the embodiment in FIGS. 1-11B that contributes to the ventricular anchor being stiffer than the atrial anchor in an axially direction is that, in this embodiment, the arches in the ventricular anchor have a thickness that is greater than the thickness of each of atrial frames 122 and 222, and thus the thickness of the arches in the two atrial frames. In this embodiment, however, the thickness of the atrial anchor at the location where the frames overlap is thicker than the thickness of the ventricular arches due to the double layer of material at the overlapping locations. In some merely exemplary embodiments the ventricular arches are 0.3 mm to 0.35 mm thick, which can be provided by cutting the ventricular anchor portion from a sheet of material that is 0.3 mm to 0.35 mm thick. In some embodiments the atrial anchor frames, and thus the arches, are 0.2 mm to 0.25 mm thick.

An additional aspect of the embodiment in FIGS. 1-11B that contributes to the ventricular anchor being stiffer than the atrial anchor is that the ventricular anchor is formed integrally with the central portion, whereas the atrial anchor portion is made from different starting material and then attached to the central portion. While this embodiment includes two different frames in the atrial anchor portion, in some embodiments the atrial anchor includes only one of the frames. For example, in some alternate embodiments, there is only one atrial frame, which comprises a plurality of peaks and valleys. In these alternative embodiments, while there are not any overlapping arches and thus no relative movement between overlapping arches, the ventricular anchor is still stiffer than the atrial anchor, in part due to the points of attachment between the central portion and the atrial anchor, and because the ventricular anchor has thicker arches than the arches of the atrial anchor.

In some alternative embodiments the ventricular anchor arches have the same thickness as the atrial arches, but the integral formation of the ventricular arches with the central portion can provide for the increased stiffness relative to the atrial arches. Additionally, even in designs where there is only one atrial anchor frame, the ventricular arches can have the same thickness as the atrial arches, and the greater stiffness of the ventricular arches is due at least partially to the integral formation of the ventricular anchor and the central portion.

In alternative embodiments, the ventricular anchor, central portion, and atrial anchor (regardless of the number of atrial frames) are all integral, but the ventricular arches are thicker than the atrial arches. In one exemplary method of manufacturing, the entire anchor could be integral and cut from a tube, but the central and atrial portions could be ground down to have a smaller thickness than the ventricular portion. Thus even though the three portions of the expandable anchor are all integral, the ventricular side is still stiffer in the axial direction due at least partially due to the thicker ventricular arches.

In some embodiments the ventricular portion, central portion, and atrial portion all have different thicknesses. For example, each of the three portions could be made from different starting materials (i.e., non-integral) with different thicknesses, and then secured together. Alternatively, the three portions could be integral and cut from a tube, and then one or more portion could be ground down to achieve a desired thickness in each portion, wherein the end result is that the three sections can have any desired thickness, such as three different thicknesses.

Some of the increased flexibility (less stiff) of the atrial arches is also due to the length of the atrial arches (the linear distance between valleys of the atrial arches) compared to the lengths of the ventricular arches (the linear distances between valleys of the ventricular arches). Ventricular valley linear distance "VV" is shown in FIG. 3, and atrial valley linear distance "AV" can be seen in FIG. 7A. In the embodiments shown herein the ventricular valley distance is less than the atrial valley distance (for both of the atrial frames in this embodiment).

In some embodiments the height of the ventricular arches "VH" (shown in FIG. 3), before the outward flare is imparted to the arches, is greater than VV. In some embodiments the two distances are substantially the same.

The embodiment in FIGS. 1-11B is also an example of a self-expandable anchor comprising a ventricular anchor integral with a central portion, and an atrial anchor secured to the central portion but not integral with the central portion. In this embodiment the expandable anchor (excluding the struts), when in an expanded configuration (which can be self-expandable) has a length L, which can be seen in FIG. 2. Midline, or half the length, is indicated as "M" in FIG. 2. In this embodiment the atrial anchor is disposed solely on the atrial side of the midline. That is, the atrial anchor portion is secured to the central portion on an atrial side of the expandable anchor. In this embodiment central portion 3 defines the radially innermost portion of the expandable anchor (excluding the struts and related structure).

In alternative embodiments the ventricular anchor can similarly be non-integral with the central portion and then secured thereto. For example, the ventricular anchor can comprise a ventricular annular frame (similar to an annular atrial frame) that is secured to the central portion, such as with rivets as described with respect to some atrial annular frames herein.

In embodiments in which the atrial anchor is not integral with the rest of the anchor, and it secured to the rest of the anchor during manufacturing, the coupling between the atrial anchor and the rest of the expandable anchor can be movable or non-movable couplings. In some situations it may be desirable to have some degree of movement between the atrial anchor and the central portion at the location of the coupling(s). In some scenarios it may be desirable to limit as much motion as possible at the location of the couplings. For example, when rivets are used to secure the atrial anchor to the central portion, examples of which are provided herein, the riveting process can be tailored to accommodate the desired degree of movement between the riveted components. Too much movement between components due to the coupling could, however, lead to material fatigue and failure. Movable coupling as used herein can be thought of as hinge points between two components, or hinge locations. The hinge allows for some movement between the two components, which can enhance, for example, the atrial anchor conforming to atrial tissue. In addition, an expandable anchor that is constructed from more than one component coupled at rivets or hinges may flex freely at the couplings and reduce ultimate material strains.

Any of the central portion, the ventricular and atrial anchor portions, and the struts can be formed from different starting materials from one another (i.e., non-integral). Non-integral components can, if desired, allow the various components to be of different flexibilities and stiffnesses, and it can also provide for radial overlapping (relative to the longitudinal axis of central opening) of the components. For example, described above, the atrial anchor can be configured to be more flexible (less stiff) than the ventricular anchor to provide better conformability and sealing in the atrium, while the stiffer ventricular anchor can provide sufficient resistance to pressure in the ventricle. In some embodiments, a thicker material can be used to form the central portion and the ventricular anchor while a thinner material can be used to form the atrial anchor. For example, the ventricular anchor can have a thickness of 0.25 mm to 0.35 mm while the atrial anchor can have a thickness of 0.15 mm to 0.25 mm. Further, in some embodiments, the length of the arches of the ventricular anchor (also referred to herein as the linear distance between valleys) can be shorter than the lengths of the arches of the atrial anchor to increase the stiffness of the ventricular anchor relative to the proximal anchor. For example, in some embodiments the arches of the atrial anchor are between 25 mm and 35 mm, such as approximately 30 mm long, while the length of the arches of the ventricular anchor are between 15 and 25 mm long, such as approximately 20 mm long.

Rivets as used herein are an example of a coupler, as that term or derivatives thereof is used herein. The locations where components are secured to one another may be referred to as a coupling herein. Coupling also refers to the two components that are secured together. Riveting as used herein is an example of a method that plastically deforms a coupler to secure two or more components together at a coupling.

Figure 12:
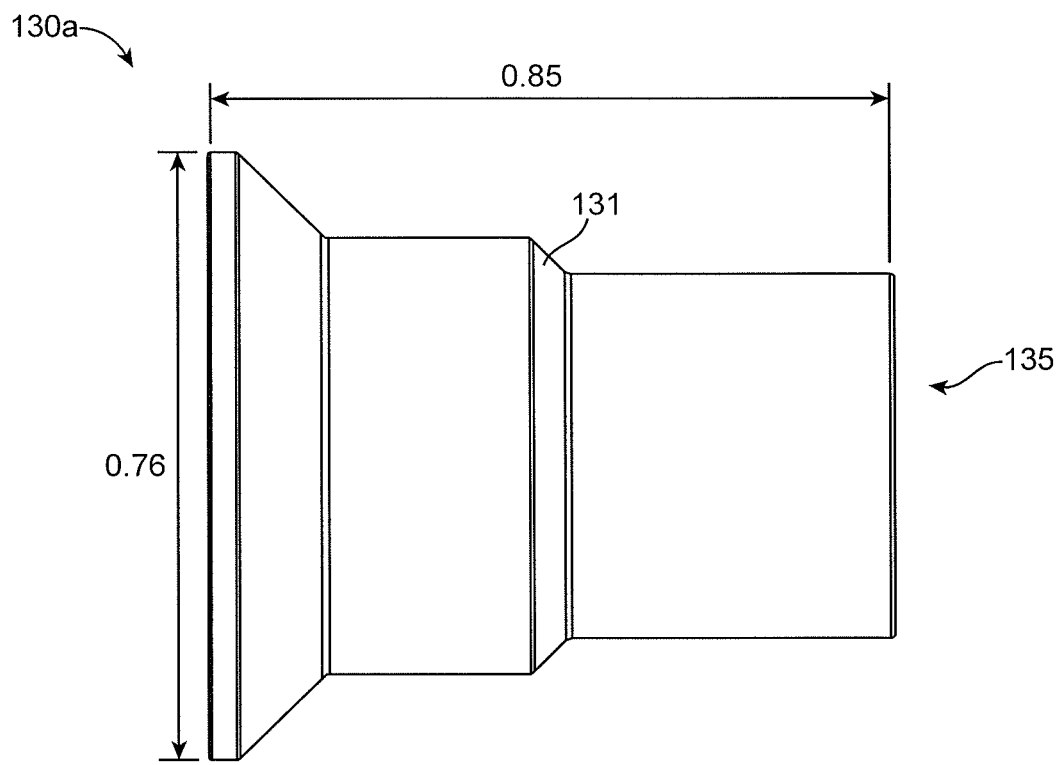
FIGS. 12 and 13 illustrate exemplary couplers.
Figure 13:
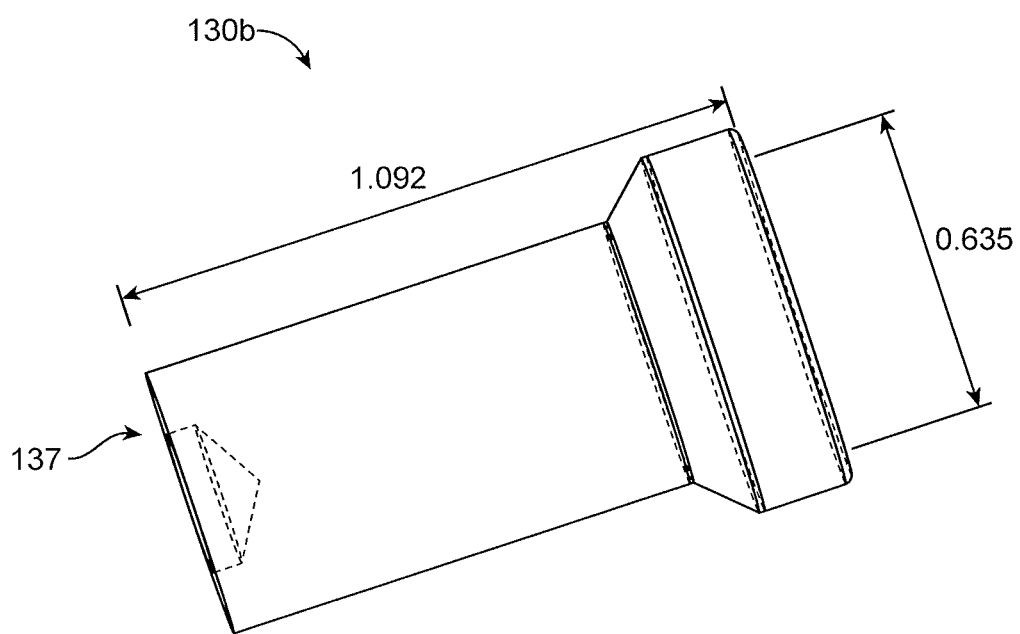

FIGS. 12 and 13 show exemplary rivets that can be used to secure two or more components together herein (including the struts described below). Rivet 130*a* as shown in FIG. 12 is a stepped rivet and rivet 130*b* as shown in FIG. 13 is a straight rivet. The rivets can be inserted through the apertures described herein and the second ends 135 and 137, respectively, can then be plastically deformed using known riveting techniques to secure the two or more components together. The rivets can be made of a suitable implantable material, such as platinum, platinum-iridium alloy, tantalum, nickel-titanium alloy, or titanium and titanium alloys, such as titanium 6-4eli. In some embodiments, the riveted coupling can be such that one or more rivets are not tightened all the way down to the secured components, which allows for hinging of the coupling, if desired. Rivets used for hinging may be made of materials suitable for implantable bearing surfaces such as Nitronic 60 alloy, or nitinol. Hinge pins can be coated with low-friction, high-durability coatings, such as diamond-like coating, or titanium nitride. Referring to FIG. 13, a stepped rivet can be used as a hinge pin. The stepped rivet can include a step, or change of diameter section 131, such that one attached component can ride along a portion of the step. In some embodiments, hinge pins can be used to attach the atrial anchor, thereby providing more flexibility for the atrial anchor. Riveting and hinging can advantageously provide for better collapsing for delivery, including a smaller delivery profile, the advantages of which are described herein, such as for transseptal access to the mitral valve. Exemplary dimensions of rivets are shown in FIGS. 12 and 13, in millimeters.

Use of rivets and hinges (as opposed to, for example, crimp tubes) can provide an additional benefit of preventing cracking that can occur as single pieces of material flex and move. Additionally, rivets and hinges can provide various degrees of relevant movement between portions of the valve, which can allow the valve to be collapsed into a smaller delivery profile for delivery. The relative movement can also provide increased flexibility of the valve during delivery. Rivets can also allow for a variation in the relative orientation of the riveted components. In some embodiments, rivets provide increased flexibility that allows for greater trackability during delivery and better self-centering of the anchor against cardiac tissue (i.e., provides advantages for both access and conformability to the anatomy).

The couplings herein (e.g., riveting) also allow different section of material with different physical properties to be secured to one another. This allows different sections of the expandable anchor to have different properties (e.g., stiffness) than other sections, as may be needed based on, for example, anatomical requirements. For example, atrial anchors can be made thinner than the central portion and/or ventricular anchors.

Figure 14:
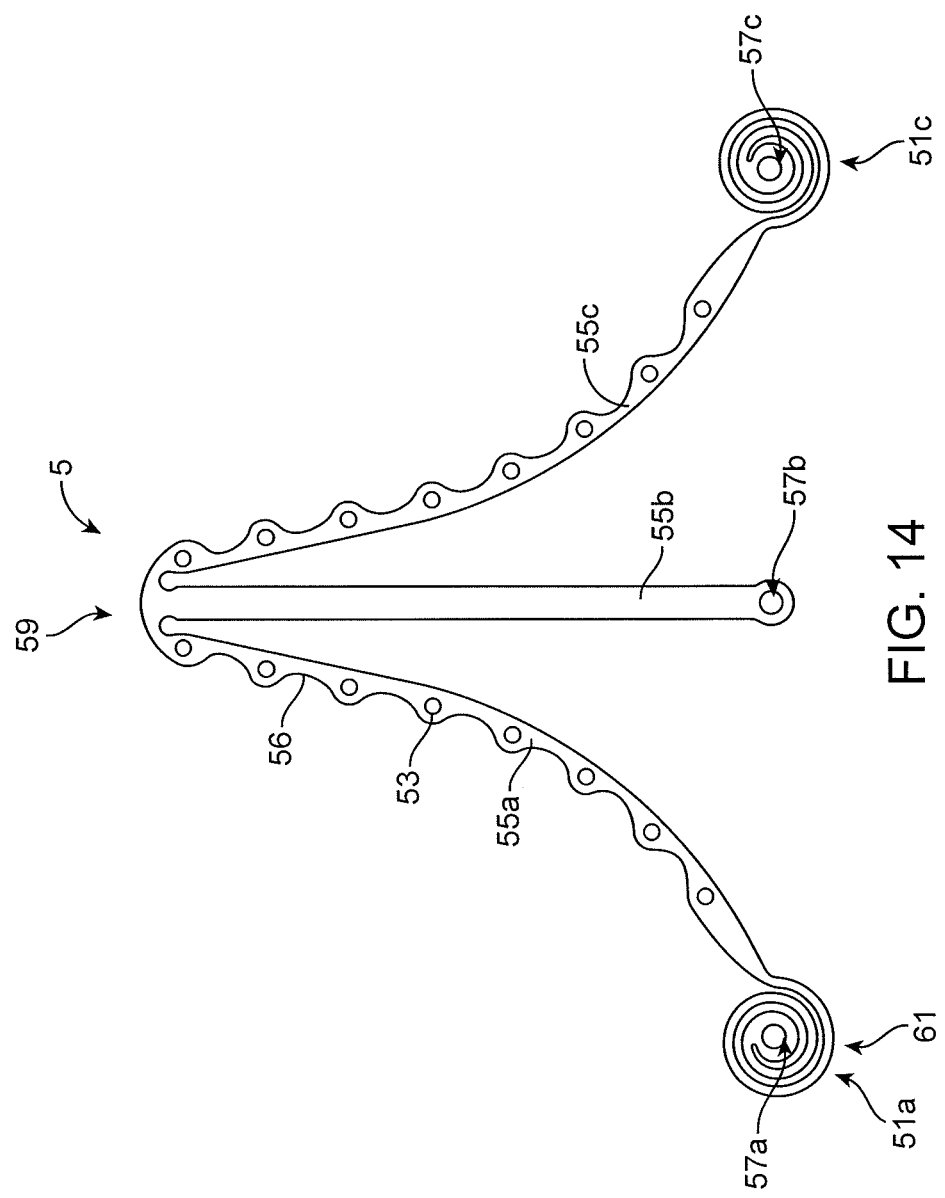
FIG. 14 illustrates an exemplary strut.
Figure 15:
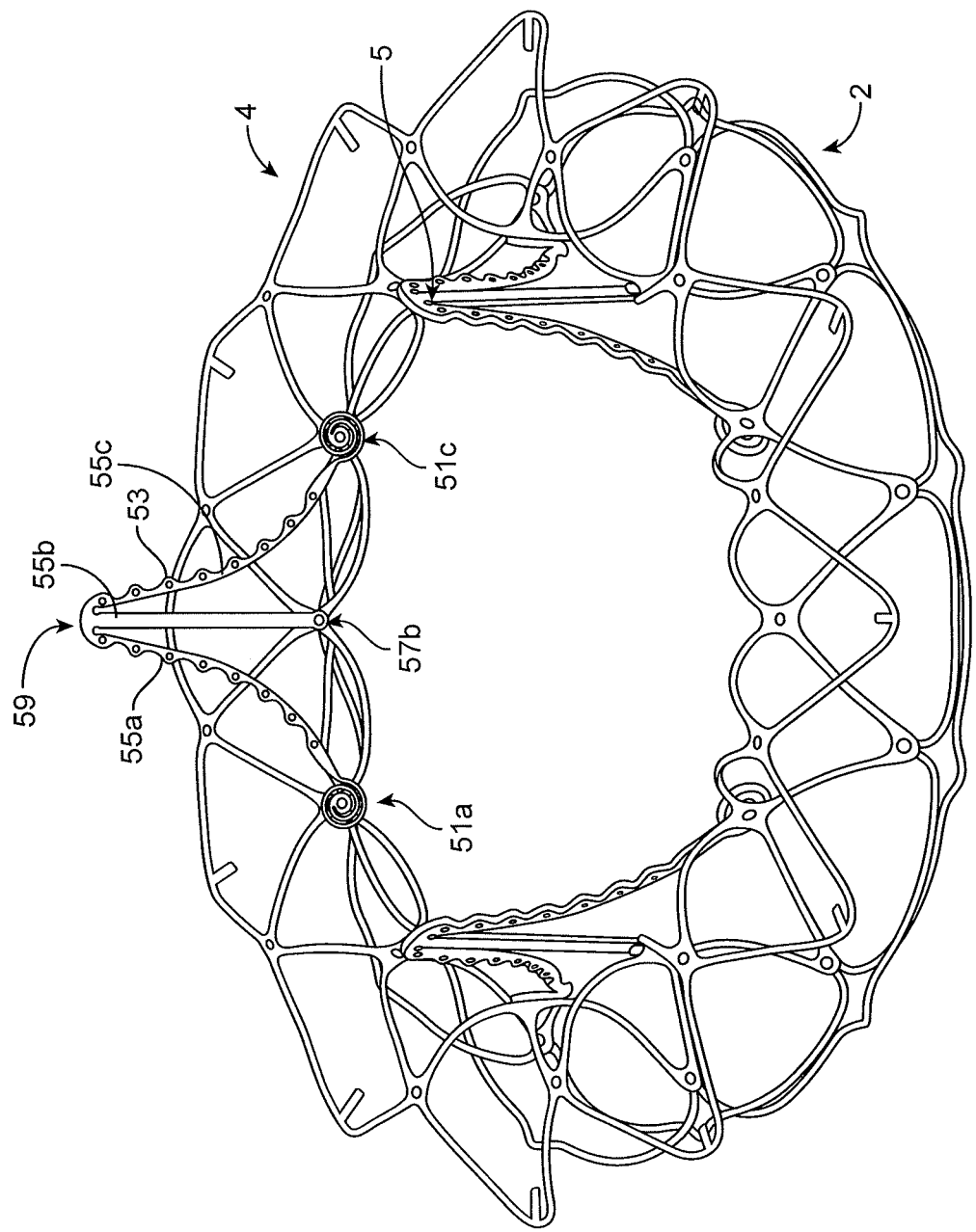
FIG. 15 illustrates an exemplary expandable anchor with three struts secured thereto.

The prostheses herein also include a plurality of struts, to which are attached replacement leaflets, which are configured to control blood flow therethrough. FIGS. 1 and 15 are perspective views illustrating three struts 5 that are individually secured to central portion 3 of the expandable anchor, and are extending distally (towards the ventricular anchor). FIG. 1 is a view from the atrial side to the ventricular side, while FIG. 12 is a view from the ventricular side to the atrial side. FIG. 14 illustrates one of the three struts 5 in the embodiment in FIGS. 1 and 12. In this exemplary embodiment three individual struts 5 are secured to central portion 3 at riveted couplings, in the same general manner as how the atrial anchor can be secured to the central portion, as described herein. Struts 5 have a ventricular end 59 and an atrial end 61, as shown in FIG. 14. Atrial end 61 includes a plurality of apertures 57a, 57b, and 57c, which are configured to be secured to apertures 36 in the central portion, such as using rivets or hinge pins as described herein. Struts 5 includes three elongate portions 55a, 55b, and 55c, each extending from ventricular end 59 and each of which has a free end at the atrial end 61. The free ends include the apertures 57a-c. Elongate portion 55b has a straight configuration, while elongate portions 55a and 55c are curved and flared outward relative to elongate portion 55b. Struts 5 have a generally triangular configuration, pointing in the distal direction. The triangular struts 5 can provide vertical strength and lateral flexibility. Elongate portions 55a and 55c are curved and have a longer overall length than the middle straight elongate portion 55b so as to provide an arched shape that lowers stress along the leaflets. Further, the atrial ends 61 of each outer elongate portion 55a and 55c can include a spring 51a and 51c, respectively, such as a clock spring, that is configured to compensate for the difference in lengths of elongate portions 55a, 55b, and 55c when the prosthesis 1 is collapsed inwards into a collapsed configuration. The curved elongate portions 55a and 55c further include suture holes 53 and/or striations or bumps 56 along the outer perimeter to provide suture attachment points for the leaflets. The struts herein can be, for example, cut from flat metal sheet or tubing.

FIG. 15 shows three struts 5 from FIG. 11 coupled to central portion 3. FIG. 15 shows the subassembly from FIG. 1, but the view in FIG. 15 is from the ventricular side looking towards the atrial side.

As shown in FIG. 15, struts 5 are attached to central portion 3 with the struts extending distally. In some embodiments there can be three struts 5 located approximately 120 degrees away from one another around the circumference of the central portion. In other embodiments, the three strut legs may be located 90 degrees apart from each other with 30 degree gaps between the legs of adjacent three strut legs.

Figure 16:
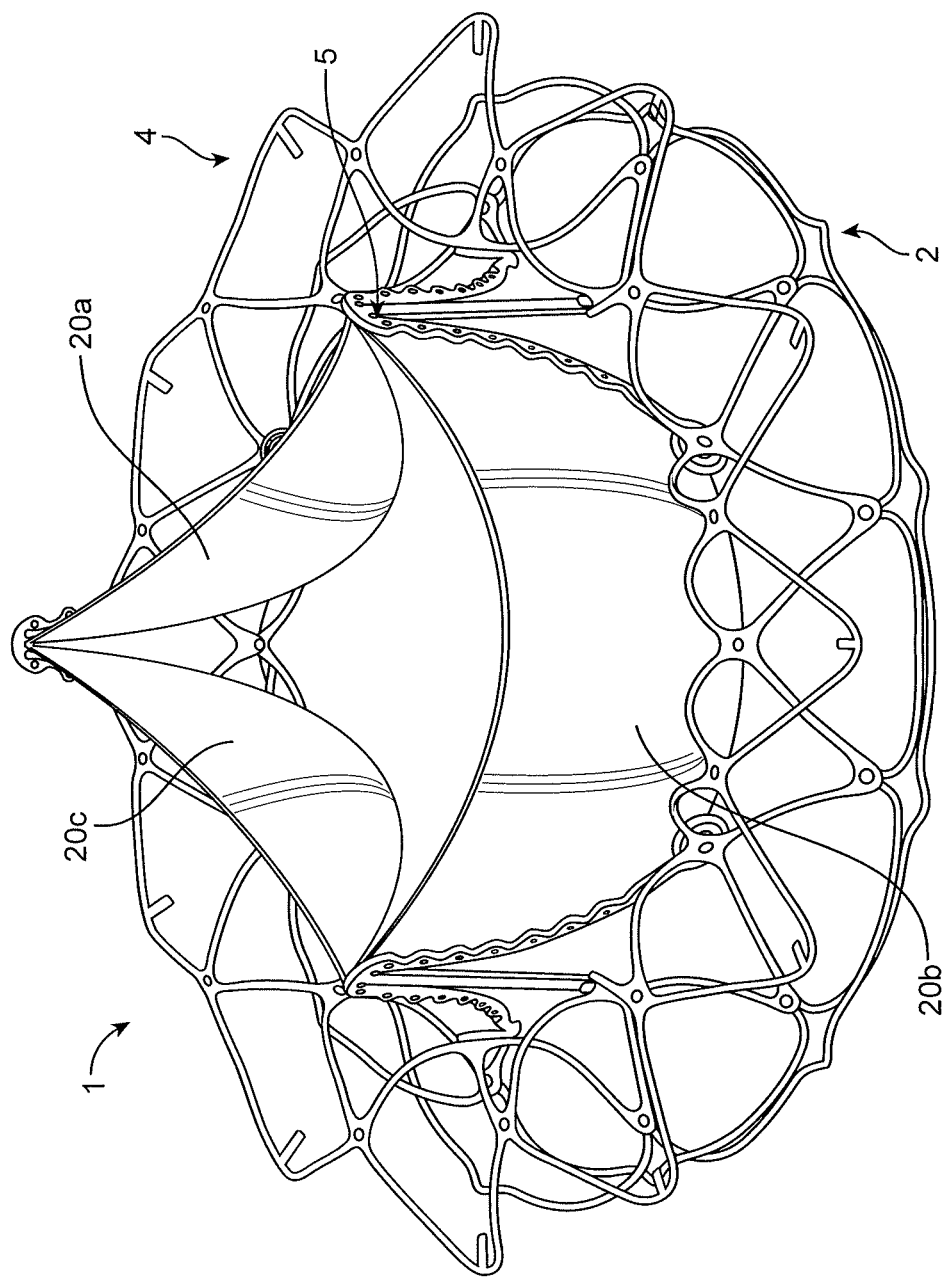
FIG. 16 illustrates an exemplary prosthesis including leaflets.

Referring to FIGS. 16 and 2, in some embodiments, the valve prosthesis 1 can include valve leaflets 20a, 20b, and 20c attached, such as sewn, to struts 5. There can be three integral valve leaflets 20a, 20b, and 20c, and the leaflets can form a pressure actuated valve that provides uni-directional flow occlusion when the prosthesis 1 is implanted in a valve orifice. The leaflets 20a-c can be constructed of bio-materials, such as bovine or porcine pericardium, or polymer materials.

Figure 17:
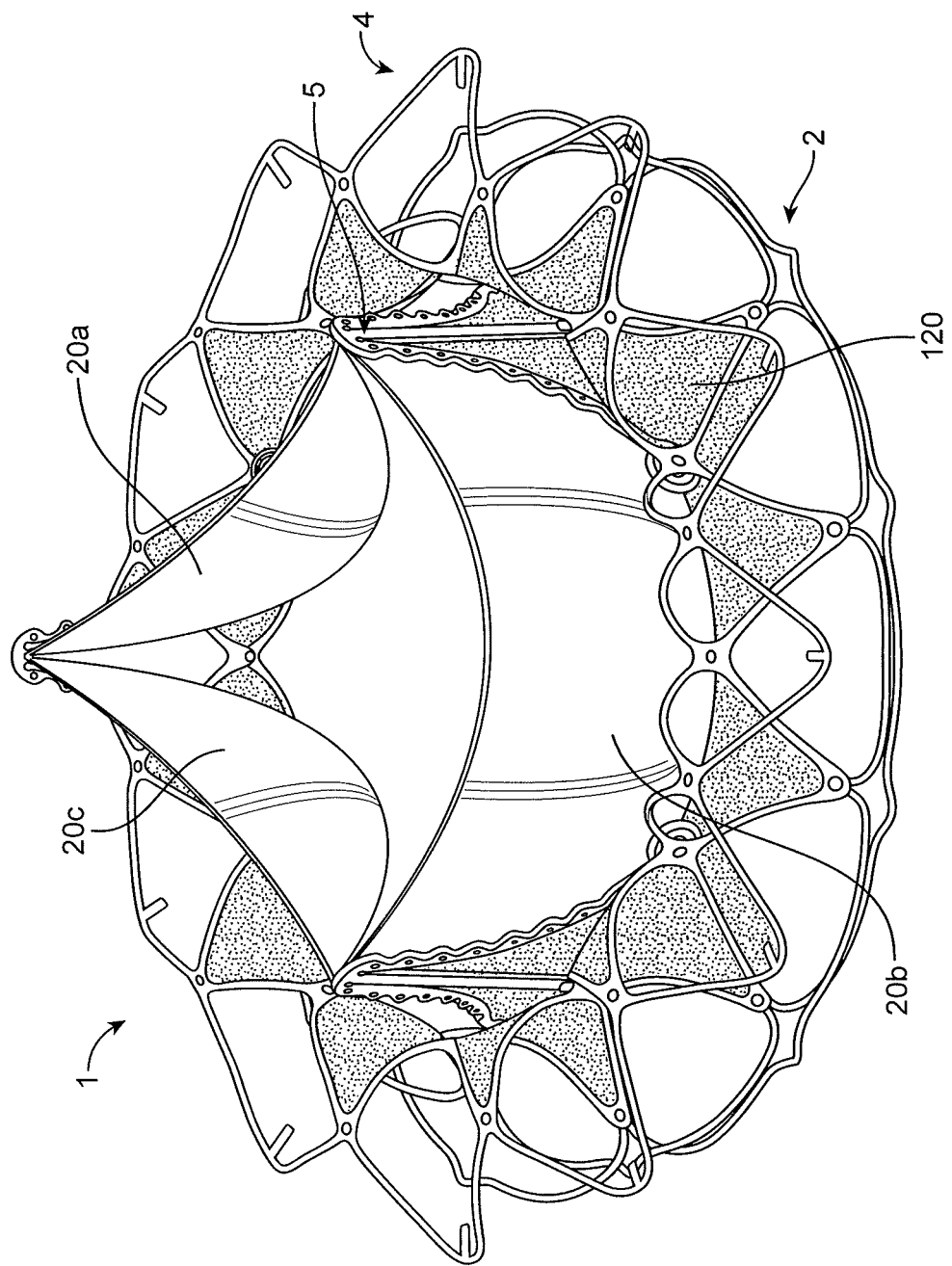
FIG. 17 illustrates a prosthesis including leaflets and an atrial skirt.

FIG. 17 illustrates central portion 4 comprising optional skirt 120 thereon or therearound formed of a biomaterial or thin polymer material. FIG. 17 is a perspective view of an exemplary prosthesis 1 with leaflets 20a-c, and skirt 120. The skirt can advantageously help seal prosthesis 1 against the cardiac tissue when implanted. In some embodiments, the ventricular anchor can include a skirt in place of, or in addition to, the skirt 120 on central portion 3. Additionally, a skirt can optionally be on the atrial anchor portion as well.

Figure 18:
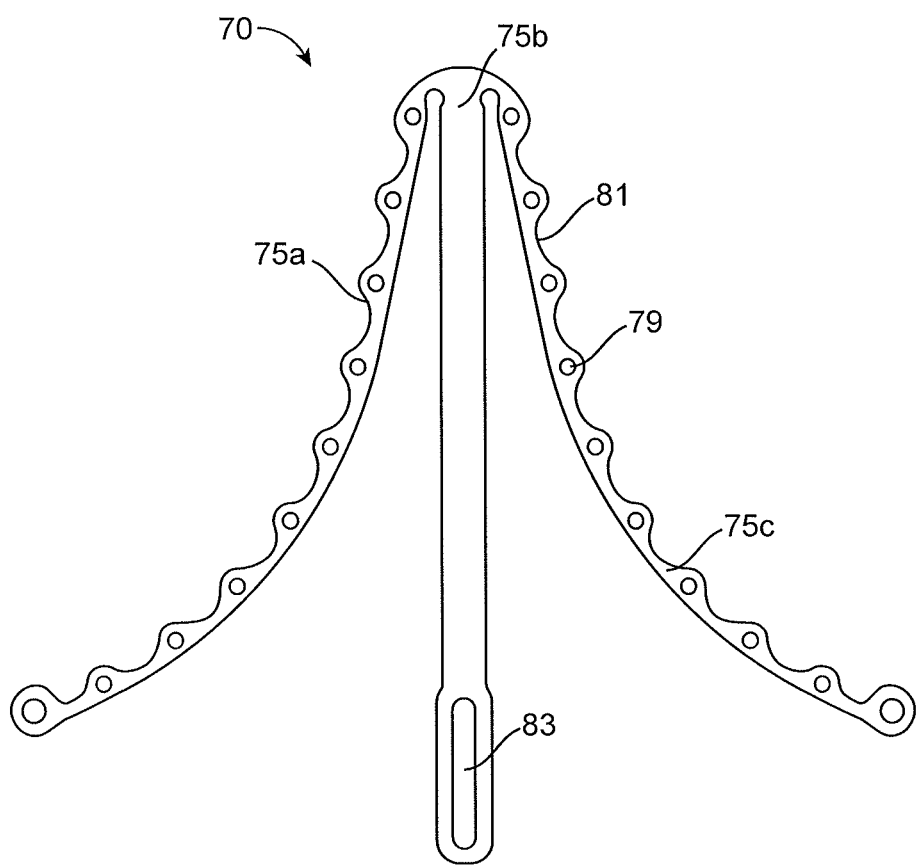
FIG. 18 illustrates an exemplary sliding valve strut.

FIG. 18 illustrates an exemplary strut 70. As shown in the embodiment of strut 70 in FIG. 18, a pin and slot mechanism (i.e., having an axially extending slot 83 along the middle elongate component 75b), could be used to make up for the differences in the lengths of elongate portions 75a-c during collapse.

Some central portions herein or other portions of other replacement heart valves may be susceptible to undesirable deforming when implanted, such as due to movement during the heartbeat and/or in response to pressures in the heart. In some embodiments the expandable anchor includes an annular strut frame coupled to a radially inner portion of the central portion (i.e., within the central portion). An annular strut frame may distribute forces more evenly over the central portion of the expandable anchor and may reduce the likelihood of undesirable central portion deformation once implanted.

An annular strut frame, if used, is an additional layer of material secured to the radially inner portion of the central portion, which reinforces and stabilizes the central portion when implanted. Additionally, by creating a coupling between the struts and the central portion (as opposed to having a solid portion of material that can provide additional stability), the flexibility of the coupling allows for relative movement of the struts during collapse of the device. This can reduce stresses on the device as it is collapsed, allowing for a smaller delivery profile, which as discussed herein can be important for delivery, such as a transseptal approach. The term annular in this context does not require a perfect annulus.

When the prosthesis includes a strut frame, the struts can either be integral to the strut frame or they can be separate components that are secured to the strut frame during manufacturing.

Figure 19:
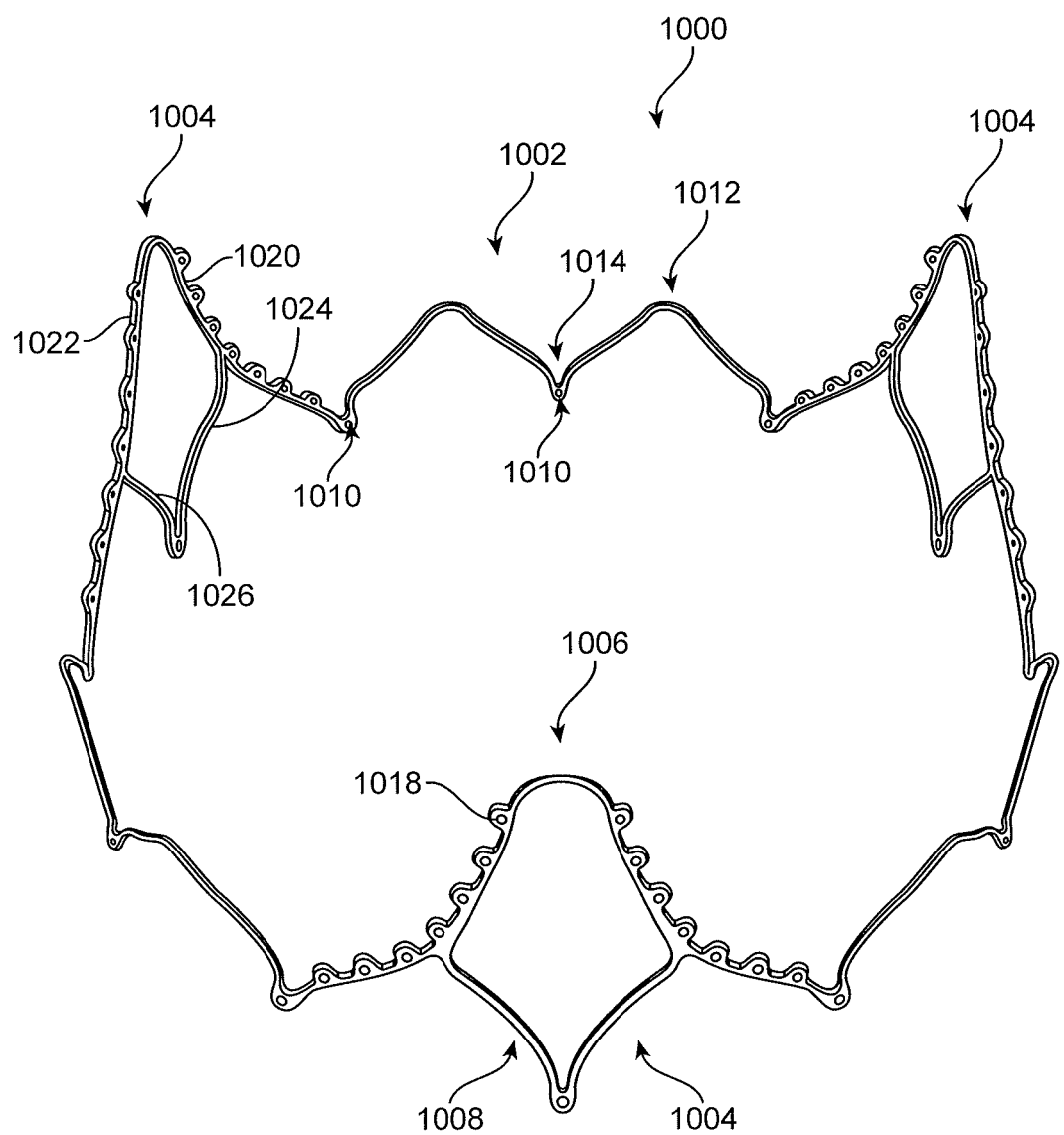
FIG. 19 illustrates an exemplary strut frame, including a plurality of struts.

FIG. 19 is a perspective view illustrating an exemplary annular strut frame 1000. Strut frame 1000 includes frame portion 1002 and plurality of struts 1004. Struts 1004 extend further distally (i.e., in the ventricular direction) than frame portion 1002, and are configured to be secured to replacement leaflets as described herein. The strut frame 1000 has a ventricular end 1006 and an atrial end 1008. Strut portion 1002 includes a plurality of arches, which define peaks 1012 and valleys 1014. In this embodiment there are six strut frame arches, with two between adjacent struts 1004. Struts 1004 have an arch configuration defined by first leg 1020 and second leg 1022, each of which has a plurality of suture apertures 1018 therein. Struts 1004 each also have first and second extensions 1024 and 1026 extending away from legs 1020 and 1022 and towards atrial end 1008. Extensions 1024 and 1026 may also be considered part of the frame portion rather than the struts. Replacement leaflets are secured to struts 1004 at holes 1018 (e.g., by suturing). The strut frame also includes a plurality of apertures 1010 near the atrial end 1008, which are used to secure the annular strut frame to the central portion of the expandable anchor. The apertures are located at valleys 1014 in the frame portion. In some embodiments the annular strut frame is positioned radially within the central portion so that each of apertures 1010 is aligned with an aperture in the central portion, such as apertures 36. A coupler (e.g., rivet) is then advanced through the aligned apertures and one side of the coupler is then plastically deformed to secure the annular strut frame to the central portion.

Figure 20:
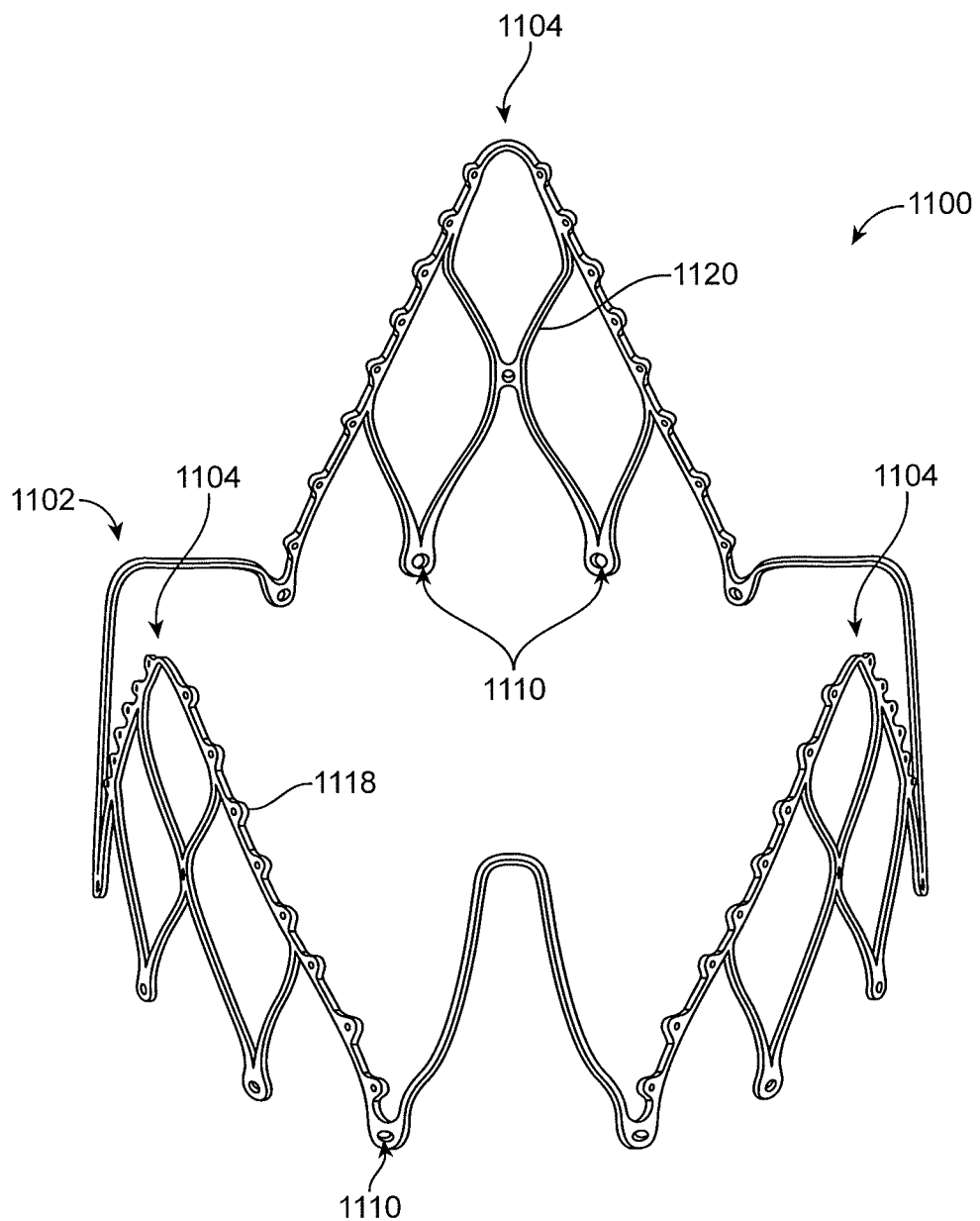
FIG. 20 illustrates an exemplary strut frame, including a plurality of struts.

FIG. 20 illustrates an exemplary annular strut frame 1100. Strut frame 1100 includes three struts 1104 and frame portion 1102, which in this embodiment includes one arch between adjacent struts 1104. Unlike the embodiment in FIG. 19, in which there is one coupling aperture 1010 within each strut, in this embodiment there are two apertures 1110 within each strut 1104. Just as in the embodiment in FIG. 19, there are also apertures at the ends of each leg of struts. Strut frame 1100 is coupled to a central portion by aligning apertures 1110 with apertures in the central portion, such as aperture 36, and then extending a coupler through each set of aligned apertures, and plastically deforming each coupler to secure the central portion to the annular strut frame at the locations of the couplings.

FIGS. 19 and 20 illustrate exemplary strut frames in their expanded configurations, when the rest of the expandable anchor (e.g., ventricular anchor, central portion, and atrial anchor) is also in an expanded configuration. Strut frames 19 and 20 can be secured to, and considered part of, any of the expandable anchors herein.

In an exemplary method of manufacturing, the strut frame is cut from a tubular element, then expanded, and set in the expanded configuration using shape setting techniques described herein or otherwise known. For example, in an exemplary embodiment, the frame is cut from a 10 mm diameter tube, then expanded to an expanded configuration of about 32 mm (as shown in FIG. 19), and set in the expanded configuration. In some exemplary embodiments the strut frames herein are 0.25 mm to about 0.45 mm thick, such as about 0.35 mm thick.

The annular strut frame can be cut from a flat sheet and rolled up and secured together (examples of which are described above), or it can be cut from a tubular structure.

FIGS. 19 and 20 illustrate exemplary annular, or cylindrical, strut frames that are disposed radially within the central portion of the expandable anchor. The central portion and the strut frame can be thought of as creating a composite cylinder when they are coupled together. The composite cylinder is thicker than each of the central portion and strut frame individually. Each of the central portion and strut frame is, however, relatively thin and can flex with respect to the other component. The relative flexibility can make it easier to collapse into a delivery configuration. If the composite region were a single material with a thickness equivalent to the combined thickness of the central portion and strut frame, that modified region may not be able to collapse sufficiently to meet, for example, size constraints without overstraining. The central portion and strut frame acting as a composite structure will not overstrain when collapsed into a collapsed configuration since the central portion and strut frame can flex independently. The composite central portion and strut frame also, when the expandable anchor expands, has a thickness greater than each component individually, thus providing an increased thickness that may be needed to resist torqueing and other forces on the central portion when implanted. The composite central portion and cylindrical strut frame thus enables collapsing as needed without overstraining, as well as provides a thickness to the central region that resists torqueing and deformation due to forces acting on the expandable anchor when implanted.

In some embodiments various components of the prosthesis are described as being formed out of a flat sheet of material, but in some embodiments they can be formed out of a tubular element or other shape of material.

In some embodiments the configuration of the arches on the ventricular anchor portion might be the same as configuration shown herein (such as in FIG. 2), but the ventricular anchor portion could be a separate frame that is secured to the central portion, just as some atrial anchors are secured to the central portion in exemplary embodiments herein. Both anchors can be separate components secured to central portion (not integral with central portion), and in some embodiments both ventricular and atrial anchors can be integral with the central portion.

In some embodiments, a prosthesis can include ventricular and atrial anchor portions that are both configured like anchor portion 2 herein. For example, both the ventricular and atrial anchor portions could be frames that are secured to the central portion. In some embodiments, a prosthesis can include ventricular and atrial anchor portions that are both configured like anchor portion 4 herein.

The prostheses herein can be configured to self-expand within a cardiac valve orifice such that the central portion lines the valve orifice while the atrial and ventricular anchors sit within the chambers of the heart and pinch tissue of the orifice therebetween, securing the prosthesis in place. Methods of delivery and deployment of prostheses that are fully incorporated herein and can be used to deliver and deploy any of the prostheses herein can be found in, for example, U.S. Pat. No. 8,870,948, issued Oct. 28, 2014.

It is conceivable that the prostheses described herein can be used to replace valves other than the mitral valve, such as the aortic valve, the tricuspid valve, and the pulmonary valve.

Figure 21:
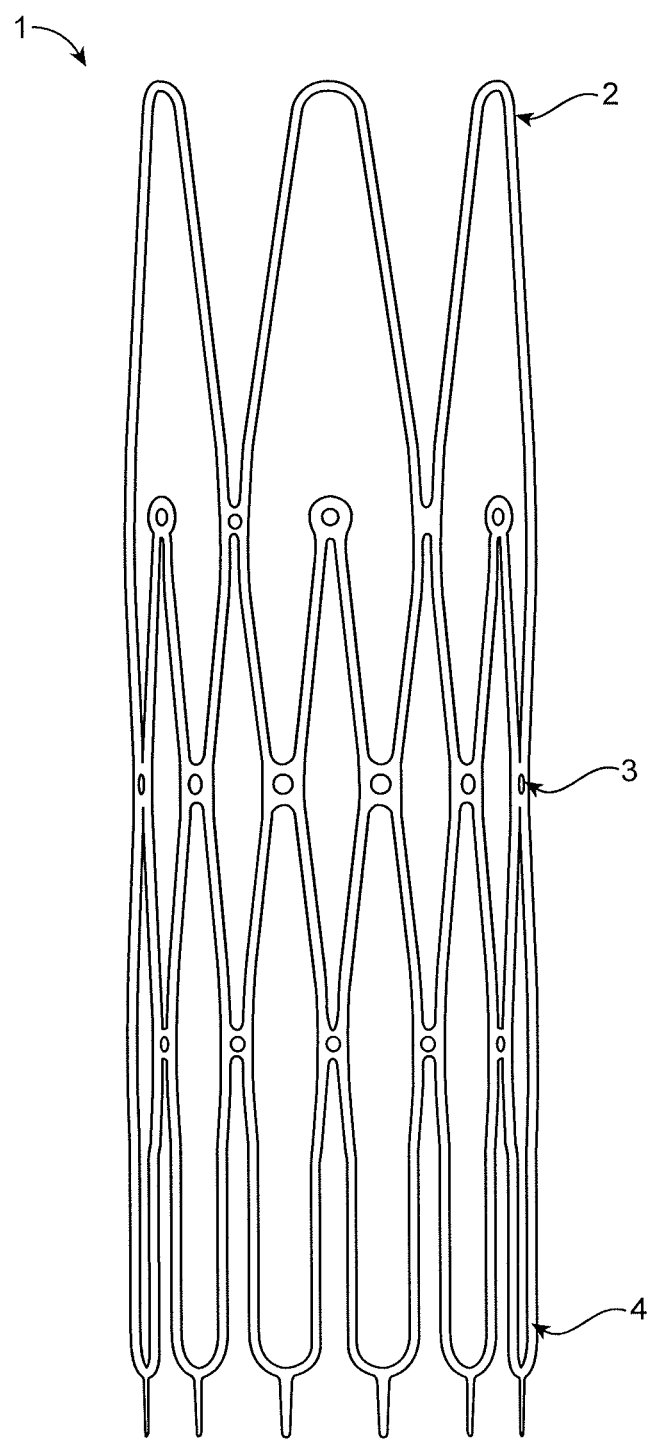
FIG. 21 represents a collapsed expandable anchor, collapsed for delivery.

FIG. 21 illustrates an exemplary configuration of a portion of expandable anchor 1 (struts and leaflets not shown for clarity) in a collapsed configuration, in which only one atrial anchor frame has been secured to central portion 3. The expandable anchor 1 can be configured to be collapsed for delivery through a catheter. In the collapsed configuration (shown in FIG. 21), the atrial and ventricular anchors 2 and 4, respectively, are extended outwards, and the entire expandable anchor can be radially collapsed. All of the arches become narrower, as do the cells in central portion 3. The expandable anchor 1 in its collapsed state can maintain a strain of less than 6% at all locations. A device and method for collapse is described in U.S. patent application Ser. No. 14/170,388, filed Jan. 31, 2014, and titled "SYSTEM AND METHOD FOR CARDIAC VALVE REPAIR AND REPLACEMENT," now U.S. Pat. No. 8,870,948, the entire contents of which are incorporated by reference herein.

One aspect of the disclosure is a replacement mitral valve, comprising: a self-expandable anchor comprising a ventricular anchor, a central portion, and an atrial anchor, the atrial anchor portion not being integral with the central portion and secured to the central portion, the self-expandable anchor having a self-expanded configuration in which the ventricular anchor and the atrial anchor are flared radially outward relative to the central portion such that the self-expandable anchor is configured to secure the replacement mitral valve to a mitral valve annulus in the self-expanded configuration, wherein the atrial anchor includes a frame having a plurality of arches and a plurality of apertures therethrough, and wherein the central portion includes a plurality of apertures therethrough, at least some of which are in alignment with one of the plurality of frame apertures; securing the frame to the central portion by extending a coupler through a central portion aperture and a frame aperture, and plastically deforming the coupler on one side of the aligned apertures, wherein plastically deforming the coupler secures the central portion and the frame at the location of the coupler; and a plurality of replacement leaflets secured to the expandable anchor.

Any of the individual components of any prostheses herein can be interchanged with components in any other example, and the examples described herein are not limited to the specific components in those examples.

What is claimed is:

1. A replacement mitral valve having a proximal and a distal end, comprising:
a self-expandable anchor comprising a ventricular anchor, a central portion, and an atrial anchor having a first frame with a plurality of first arches and a second frame with a plurality of second arches at least a portion of which overlap the plurality of first arches at the proximal end of the replacement mitral valve, the self-expandable anchor having a self-expanded configuration in which the ventricular anchor and the atrial anchor are flared radially outward relative to the central portion and relative to a longitudinal axis of the device such that the replacement mitral valve is configured to be secured within a mitral valve orifice, the ventricular anchor having a ventricular stiffness at radial outer portion of the ventricular anchor in a direction parallel to the longitudinal axis when the expandable anchor is in the self-expanded configuration and the atrial anchor having an atrial stiffness at radial outer portion of the atrial anchor in a direction parallel to the longitudinal axis when the expandable anchor is in the self-expanded configuration, the ventricular stiffness greater than the atrial stiffness; and
a plurality of replacement leaflets secured to the expandable anchor.

2. The replacement mitral valve of claim 1 wherein the ventricular anchor has a plurality of ventricular arches with a first thickness, either one of the plurality of first arches and plurality of second arches has a second thickness less than the first thickness, and wherein the thickness dimensions is measured radially when the expandable anchor is in a collapsed configuration.

3. The replacement mitral valve of claim 2, wherein the second thickness being the thickness of the plurality of first arches, the plurality of second arches having a third thickness less than the first thickness.

4. The replacement mitral valve of claim 3 wherein the second thickness is the same as the third thickness.

5. The replacement mitral valve of claim 1, the ventricular anchor having a plurality of ventricular arches with ventricular peaks and valleys, the first frame with the a plurality of first arches includes atrial peaks and valleys, the linear distance between ventricular valleys being less than the linear distance between atrial valleys, when the expandable anchor is in the expanded configuration.

6. The replacement mitral valve of claim 5 wherein the second frame with the plurality of second arches includes peaks and valleys, the linear distance between ventricular valleys also being less than the linear distance between valleys of the second frame.

7. The replacement mitral valve of claim 1, the ventricular anchor having a plurality of ventricular arches with ventricular peaks and the atrial anchor having a plurality of atrial arches defining atrial peaks, wherein midpoints of the ventricular peaks have greater stiffness in the axial direction than midpoints of the atrial peaks.

8. The replacement mitral valve of claim 1 wherein the plurality of ventricular arches are stiffer than each of the first arches and the second arches in the axial direction.

9. The replacement mitral valve of claim 1 having a ventricular end and an atrial end, the two ends being the radially outermost points of either side of a midline of the expandable anchor when the anchor is in the expanded configuration.

10. The replacement mitral valve of claim 1 wherein the ventricular anchor comprises, when the expandable anchor is in a collapsed configuration, a plurality of triangular arches pointing towards a ventricular end of the replacement mitral valve, and the central portion comprises a plurality of triangular central arches pointing towards an atrial end of the replacement mitral valve.

11. The replacement mitral valve of claim 1 wherein at least a portion of the plurality of first arches and at least a portion of the plurality of second arches each comprise a protuberance at a midpoint of the arch.

12. The replacement mitral valve of claim 1 wherein the ventricular anchor comprises a plurality of arches having triangular configurations.

13. The replacement mitral valve of claim 12 wherein the plurality of arches define a plurality of peaks and a plurality of valleys, the height of the peaks being greater than the linear distance between adjacent valleys, the height being measured orthogonal to the linear distance between adjacent valleys.

14. The replacement mitral valve of claim 13 wherein the ventricular anchor comprises a plurality of arches each having the same triangular configuration with a rounded end.

15. The replacement valve of claim 1 further comprising a plurality of struts secured to the self-expandable anchor and the replacement leaflets.

16. The replacement valve of claim 15 further comprising a cylindrical strut frame secured to the self-expandable anchor, the strut frame comprising the plurality of struts.

17. The replacement valve of claim 16 wherein the strut frame is secured to the central portion of the expandable anchor.

18. The replacement valve of claim 17 wherein the strut frame includes a plurality of apertures and the central portion comprises a plurality of apertures, each of the plurality of apertures on the strut frame is aligned with an aperture on the central portion, the central portion secured to the strut frame at the location of the aligned apertures.

19. A replacement mitral valve, comprising:
a self-expandable anchor comprising a ventricular anchor, a central portion, and an atrial anchor, the self-expandable anchor having a self-expanded configuration in which the ventricular anchor and the atrial anchor are flared radially outward relative to the central portion such that the replacement mitral valve is configured to be secured within a mitral valve orifice, wherein the ventricular anchor has a plurality of ventricular arches defining ventricular peaks and valleys and the atrial anchor has a plurality of atrial arches defining atrial peaks and valleys, a ventricular linear distance between ventricular valleys being less than an atrial linear distance between atrial valleys and a ventricular height from ventricular valleys to ventricular peaks being less than an atrial height between atrial peaks and atrial valleys when the expandable anchor is in the expanded configuration such that the ventricular arches are stiffer than the atrial arches;

a cylindrical strut frame disposed radially within and secured to a radially inner portion of the self-expandable anchor;

a plurality of attachment elements connecting the cylindrical strut frame to the expandable anchor; and a plurality of replacement leaflets secured to the self-expandable anchor.

20. The replacement mitral valve of claim 19 wherein the atrial anchor is secured to the central portion but not integral with the central portion and the ventricular anchor is integral with the central portion.

21. The replacement mitral valve of claim 20 wherein the atrial anchor is secured to the central portion at a plurality of couplings.

22. The replacement mitral valve of claim 21 wherein the atrial anchor comprises an annular frame, and wherein the annular frame is secured to the central portion at a plurality of couplings.

23. The replacement mitral valve of claim 22 wherein the atrial anchor comprises a second annular frame, wherein the second frame is secured to the central portion at a second plurality of couplings.

24. The replacement mitral valve of claim 23 wherein the first and second plurality of coupling are movable couplings between the central portion and the first and second frames at the location of the first and second plurality of couplings.

25. The replacement mitral valve of claim 24 wherein the first and second couplings alternate around a longitudinal axis of the central portion.

26. The replacement mitral valve of claim 19, wherein struts of each of the ventricular arches have a first thickness and struts of each of the atrial arches have a second thickness less than the first thickness, wherein the thickness dimension is measured radially when the expandable anchor is in a collapsed configuration.

27. The replacement mitral valve of claim 19 wherein the atrial arches are part of a first frame, the atrial anchor further including a second frame with a plurality of second arches defining peaks and valleys, at least one of the atrial arches overlaps with one of the plurality of second arches, the linear distance between ventricular valleys also being less than the linear distance between valleys of the second frame.

28. The replacement mitral valve of claim 19, wherein midpoints of the ventricular peaks have greater stiffness in the axial direction than midpoints of the atrial peaks.

29. The replacement mitral valve of claim 19 wherein the ventricular anchor comprises, when the expandable frame is in a collapsed configuration, a plurality of triangular arches pointing towards a ventricular end of the replacement mitral valve, and the central portion comprises a plurality of triangular central arches pointing towards an atrial end of the replacement mitral valve.

30. The replacement mitral valve of claim 19 wherein the atrial anchor includes a first frame with a plurality of first arches and a second frame with a plurality of second arches, at least a portion of the plurality of first arches overlapping with a portion of the plurality of second arches.

31. The replacement mitral valve of claim 30 wherein at least a portion of the plurality of first arches and at least a portion of the plurality of second arches each comprise a protuberance at a midpoint of the arch.

32. The replacement mitral valve of claim 19, wherein the ventricular height is greater than the ventricular linear distance when the expandable anchor is in the expandable configuration.

* * * * *